(12) United States Patent
Rafalko et al.

(10) Patent No.: US 10,449,149 B2
(45) Date of Patent: Oct. 22, 2019

(54) PHARMACEUTICAL PREPARATION OF CARBOHYDRATES FOR THERAPEUTIC USE

(71) Applicant: Glycomine, Inc., San Carlos, CA (US)

(72) Inventors: Agnes Rafalko, San Francisco, CA (US); Tatyana Chernenko, San Jose, CA (US)

(73) Assignee: Glycomine, Inc., San Francisco, CA (US)

( * ) Notice: Subject to any disclaimer, the term of this patent is extended or adjusted under 35 U.S.C. 154(b) by 0 days.

(21) Appl. No.: 15/788,591

(22) Filed: Oct. 19, 2017

(65) Prior Publication Data

US 2018/0036239 A1  Feb. 8, 2018

Related U.S. Application Data

(63) Continuation of application No. 15/022,194, filed as application No. PCT/US2014/055921 on Sep. 16, 2014, now abandoned.

(60) Provisional application No. 61/878,591, filed on Sep. 16, 2013.

(51) Int. Cl.
*A61K 9/127* (2006.01)
*A61K 31/7028* (2006.01)

(52) U.S. Cl.
CPC .......... *A61K 9/1271* (2013.01); *A61K 9/127* (2013.01); *A61K 31/7028* (2013.01)

(58) Field of Classification Search
CPC ... A61K 9/1271; A61K 31/7028; A61K 9/127
See application file for complete search history.

(56) References Cited

U.S. PATENT DOCUMENTS

| | | | | |
|---|---|---|---|---|
| 5,013,556 | A * | 5/1991 | Woodle | A61K 9/1271 264/4.3 |
| 7,011,845 | B2 * | 3/2006 | Kozbor | A61K 9/127 424/435 |
| 2002/0072121 | A1 * | 6/2002 | Lam | A61K 9/1272 435/458 |
| 2007/0120280 | A1 | 5/2007 | Anchordoquy et al. | |
| 2009/0054353 | A1 | 2/2009 | Gravier-Pelletier et al. | |
| 2011/0200582 | A1 | 8/2011 | Baryza et al. | |
| 2011/0257233 | A1 | 10/2011 | Cosford et al. | |
| 2013/0171233 | A1 | 7/2013 | Paulson et al. | |

FOREIGN PATENT DOCUMENTS

| | | |
|---|---|---|
| WO | 2007/096532 A1 | 8/2007 |
| WO | 2009/118658 A2 | 10/2009 |

OTHER PUBLICATIONS

Eklund et al., "Hydrophobic Man-1-P Derivatives Correct Abnormal Glycosylation in Type I Congenital Disorder of Glycosylation Fibroblasts", Glycobiology, vol. 15, No. 11, 2005, pp. 1084-1093.

International Preliminary Report on Patentability received for PCT Patent Application No. PCT/US2014/055921, dated Mar. 31, 2016, 6 pages.

International Search Report and Written Opinion received for PCT Patent Application No. PCT/US2014/055921 dated Apr. 23, 2015, 8 pages.

Alwael et al., "Liquid Chromatographic Profiling of Monosaccharide Concentrations in Complex Cell-Culture Media and Fermentation Broths", Analytical Methods, vol. 3, No. 1, Jan. 2011, pp. 62-69.

Bones et al., "Identification of N-Glycans Displaying Mannose-6-Phosphate and their Site of Attachment on Therapeutic Enzymes for Lysosomal Storage Disorder Treatment", Analytical Chemistry, vol. 83, 2011, pp. 5344-5352.

Chan et al., "A Mouse Model of a Human Congenital Disorder of Glycosylation Caused by Loss of PMM2", Human Molecular Genetics, vol. 25, No. 11, 2016, pp. 2182-2193.

Colletier et al., "Protein Encapsulation in Liposomes: Efficiency Depends on Interactions between Protein and Phospholipid Bilayer", BMC Biotechnology Electronic Resource, vol. 2, No. 9, 2002, pp. 1-8.

Eklund et al., "Congenital Disorders of Glycosylation and their Effects on the Liver", Fibrocystic Diseases of the Liver, 2010, pp. 287-317.

Extended European Search Report received for European Patent Application No. 14851464.9, dated Mar. 16, 2017, 9 pages.

Freeze et al., "Neurology of Inherited Glycosylation Disorders", The Lancet Neurology, vol. 11, No. 5, May, 2012, pp. 453-466.

Freeze, Hudson H., "Towards a Therapy for Phosphomannomutase 2 Deficiency, the Defect in CDG-Ia Patients", Biochimica Et Biophysica Acta, vol. 1792, 2009, pp. 835-840.

Fujiwara et al., "Intracellular Fate of Octaarginine-Modified Liposomes in Polarized MDCK Cells", International Journal of Pharmaceutics, vol. 386, 2010, pp. 122-130.

Gao et al., "Non-Radioactive Analysis of Lipid-Linked Oligosaccharide Compositons by Fluorophore-Assisted Carbohydrate Electrophoresis", Methods in Enzymology, vol. 415, 2006, pp. 3-20.

Garbuzenko et al., "Effect of Grafted PEG on Liposome Size and on Compressibility and Packing of Lipid Bilayer", Chemistry and Physics of Lipids, vol. 135, No. 2, 2005, pp. 117-129.

Hardré et al., "Mono, Di and Tri-Mannopyranosyl Phosphates as Mannose-1-Phosphate Prodrugs for Potential CDG-Ia Therapy", Bioorganic & Medicinal Chemistry Letters, vol. 17, 2007, pp. 152-155.

Hubbard et al., "Synthesis of the N-linked Oligosaccharideos of Glycoproteins", The Journal of Biological Chemistry, vol. 255, No. 24, 1980, pp. 11782-11793.

Huwyler et al., "Receptor Mediated Delivery of Daunomycin Using Immunoliposomes: Pharmacokinetics and Tissue Distribution in the Rat1", The Journal of Pharmacology and Experimental Therapeutics, vol. 282, No. 3, 1997, pp. 1541-1546.

(Continued)

*Primary Examiner* — Snigdha Maewall
(74) *Attorney, Agent, or Firm* — Morrison & Foerster LLP

(57) ABSTRACT

The disclosure provides methods for preparation of carbohydrate replacement therapies (CRT) that include nanocarriers of carbohydrates and glycolipids for pharmaceutical delivery to cell interior, endoplasmic reticulum, and Golgi for treating CDG type I and CDG type II diseases as well as other metabolic disorders.

23 Claims, 2 Drawing Sheets

(56) References Cited

OTHER PUBLICATIONS

Immordino et al., "Stealth Liposomes: Review of the Basic Science, Rationale, and Clinical Applications, Existing and Potential", International Journal of Nanomedicine, vol. 1, No. 3, 2006, pp. 297-315.
Jaeken et al., "Congenital Disorders of Glycosylation: A Rapidly Expanding Disease Family", Annual Review of Genomics and Human Genetics, vol. 8, 2007, pp. 261-278.
Jaeken et al., "On the Nomenclature of Congenital Disorders of Glycosylation (CDG)", Journal of Inherited Metabolic Disease, vol. 31, 2008, pp. 669-672.
Kjaergaard et al., "Failure of Short-Term Mannose Therapy of Patients with Carbohydrate-Deficient Glycoprotein Syndrome Type 1A", Acta Paediatrica, vol. 87, 1998, pp. 884-888.
Körner et al., "Abnormal Synthesis of Mannose 1-Phosphate Derived Carbohydrates in Carbohydrate-Deficient Glycoprotein Syndrome Type I Fibroblasts with Phosphomannomutase Deficiency", Glycobiology, vol. 8, No. 2, 1998, pp. 165-171.
Koshkaryev et al., "Targeting of Lysosomes by Liposomes Modified with Octadecyl-rhodamine B", Journal of Drug Targeting, vol. 19, No. 8, Sep. 2011, pp. 606-614.
Leroy, Jules G., "Congenital Disorders of N-Glycosylation including Diseases Associated with O- As Well As N-Glycosylation Defects", Pediatric Research, vol. 60, No. 6, 2006, pp. 643-656.
Mayatepek et al., "Mannose Supplementation in Carbohydrate-Deficient Glycoprotein Syndrome Type I and Phosphomannomutase Deficiency", European Journal of Pediatrics, vol. 157, 1998, pp. 605-612.
Niehues et al., "Carbohydrate-Deficient Glycoprotein Syndrome Type Ib. Phosphomannose Isomerase Deficiency and Mannose Therapy", The Journal of Clinical Investigation, vol. 101, No. 7, Apr. 1998, pp. 1414-1420.
Pollock et al., "Uptake and Trafficking of Liposomes to the Endoplasmic Reticulum", The FASEB Journal, vol. 24, No. 6, 2010, pp. 1866-1878.
Rutschow et al., "Mernbrane-Permeant Derivatives of Mannose-1-phosphate", Bioorganic & Medicinal Chemistry, vol. 10, 2002, pp. 4043-4049.
Schaftingen et al., "Phosphomannomutase Deficiency is a Cause of Carbohydrate-Deficient Glycoprotein Syndrome Type I", FEBS Letters, vol. 377, 1995, pp. 318-320.
Schneider et al., "Successful Prenatal Mannose Treatment for Congenital Disorder of Glycosylation-la in Mice", Nature Medicine, vol. 18, No. 1, Jan. 2012, pp. 71-73.
Sparks et al., "Congenital Disorders of N-Linked Glycosylation and Multiple Pathway Overview", GeneReviews, Available Online at <https://www.ncbi.nlm.nih.gov/books/NBK1332/?report=printable>, Aug. 15, 2005, pp. 1-24.
Sugimoto et al., "Oligomannose-Coated Liposomes as an Adjuvant for the Induction of Cell-Mediated Immunity", FEBS Letters, vol. 363, No. 1-2, 1995, pp. 53-56.
Thiel et al., "Targeted Disruption of the Mouse Phosphomannomutase 2 Gene Causes Early Embryonic Lethality", Molecular and Cellular Biology, vol. 26, No. 15, Aug. 2006, pp. 5615-5620.
Torchilin et al., "Recent Advances with Liposomes as Pharmaceutical Carriers", Nature Reviews. Drug Discovery, vol. 4, Feb. 2005, pp. 145-160.
Torchilin et al., "TAT-Liposomes: A Novel Intracellular Drug Carrier", Current Protein and Peptide Science, vol. 4, 2003, pp. 133-140.
Wang et al., "A General Strategy for the Chemoenzymatic Synthesis of Asymmetrically Branched N-Glycans", Science, vol. 341, Jul. 26, 2013, pp. 379-383.
Weerapana et al., "Investigating Bacterial N-Linked Glycosylation: Synthesis and Glycosyl Acceptor Activity of the Undecaprenyl Pyrophosphate-Linked Bacillosamine", Journal of the American Chemical Society, vol. 127, No. 40, Oct. 12, 2005, pp. 13766-13767.
Westmark et al., "Boronic Acids Selectively Facilitate Glucose Transport Through a Lipid Bilayer", Journal of the American Chemical Society, vol. 116, No. 20, 1994, pp. 9343-9344.
Westphal, "A frequent Mild Mutation in ALG6 May Exacerbate the Clinical Severity of Patients with Congenital Disorder of Glycosylation la (CDG-Ia) caused by Phosphomannomutase Deficiency", Human Molecular Genetics, vol. 11, No. 5, 2002, pp. 599-604.

* cited by examiner

PEG-DSPE

PHARMACEUTICAL PREPARATION OF CARBOHYDRATES FOR THERAPEUTIC USE

CROSS REFERENCE TO RELATED APPLICATIONS

This application is a continuation of U.S. patent application Ser. No. 15 15/022,194, with an international filing date of Sep. 16, 2014, which is a U.S. National Phase patent application of PCT/US2014/055921, filed Sep. 16, 2014, which claims the benefit of U.S. Provisional Application No. 61/878,591, filed Sep. 16, 2013, the disclosures of which are herein incorporated by reference in their entirety.

FIELD

The present invention relates to compositions containing carbohydrates encapsulated in a lipid particle for delivery to the cell interior, methods of delivering the encapsulated carbohydrates into the interior of cells, and methods of using such compositions for treating diseases and disorders, such as congenital disorders of glycosylation (CDG). For example, the present invention relates to methods for preparation of carbohydrates and glycolipids for pharmaceutical delivery to cell interior, endoplasmic reticulum (ER), and Golgi.

BACKGROUND

Glycosylation, the enzymatic attachment of carbohydrates (glycans) to proteins and lipids is a co-translational and post-translational modification (PTM) that is more common than any other PTM as it applies to a majority of proteins synthesized in the rough endoplasmic reticulum (ER). Glycosylation plays a critical role in a variety of biological processes of membrane and secreted proteins. In the ER, glycosylation defines protein structure and folding and acts as a quality control mechanism that dictates the export of properly folded proteins to Golgi or targets misfolded ones for degradation. Glycan moieties may also act as ligands for cell surface receptors to mediate cell attachment or stimulate signal transduction pathways. Congenital disorders of glycosylation, also known as CDG syndromes, are a group of rare genetic diseases where tissue proteins and/or lipids carry defective glycosylation and/or lack of glycosylation. These diseases are linked to numerous enzymatic deficiencies and often times cause severe, sometimes fatal, impairments of the nervous system, muscles, intestines, and several other organ systems.

Common clinical symptoms in children with CDG include hypotonia, developmental delay, failure to thrive, hepatic dysfunction, coagulopathy, hypothyroidism, esotropia, abnormal fat pattern and inverted nipples, hypoglycemia, seizure, cerebellar hypoplasia, and stroke-like episodes in a developmentally delayed child. At an older age, in adolescence, and adulthood, the presentation may include ataxia, cognitive impairment, and absence of puberty in females, small testes in males, retinitis pigmentosa, scoliosis, joint contractures, and peripheral neuropathy.

CDG may be classified into two groups: CDG type I and CDG type II. CDG type I is characterized by defects in the initial steps of N-linked protein glycosylation, i.e., biosynthesis of dolichol pyrophosphate linked oligosaccharide (DLO), which occur in the ER, or transfer of the DLO to asparagine residues of nascent polypeptides. CDG type II involves defects in further processing (synthetic or hydrolytic) of the protein-bound glycan. Currently, twenty-two CDG type I and fourteen type II variants have been identified. One of the most common subtype of CDG is CDG-Ia (approximately 70% of all CDG cases), which is characterized by loss or reduction of phosphomannomutase 2 (PMM) activity leading to deficiency or insufficiency in intracellular N-glycosylation (Jaeken et al. *J. of Inherit. Met. Disease.* 2008, 31: 669-672). PMM as responsible for the conversion of mannose-6-phosphate to mannose-1-phosphate.

Although several different approaches to developing therapies for CDG have been explored, researchers continue their search for a suitable cure or a therapy for mitigating the disease itself. Existing treatments for manifestations include, for example, nutritional supplements, tube feeding, and a wide range of therapies that attempt to treat gastroesophageal reflux, persistent vomiting, developmental delays, ocular abnormalities, and hypothyroidism. Patients also require intravenous (IV) hydration and physical therapy for stroke-like episodes. Adults with orthopedic symptoms often require wheel chairs, transfer devices, and surgical treatment for scoliosis (Sparks et al., Disorders of Glycosylation Overview. 2005 in: Pagon R A, Adam M P, Bird T D, et al., editors. GeneReviews™, Seattle (Wash.): University of Washington, Seattle; 1993-2013).

Currently, CDG-Ib is the only known CDG for which a relatively effective treatment is available, namely oral D-mannose administration. However, such therapy may not be as effective in treating CDG-Ia patients and there are currently limited treatment options for other CDG type I subtypes and CDG type II diseases. One of the reasons for a lack in established therapy for CDG-I disorders may be due to the plethora of heterogeneous clinical phenotypes presented that do not show a direct correlation to the PMM enzyme activity.

Patients suffering from a reduction in PMM activity have reduced production of mannose-1-phosphate (Man-1-P), associated with symptoms of multivisceral impairments. In order to overcome PMM production deficiency, it is important to supply downstream enzymes with the required substrate (i.e., Man-1-P). However, the delivery and maintenance of such a systemic supply of Man-1-P is problematic, as extracellular enzymes within bodily fluids degrade Man-1-P when delivered exogenously by oral or intravenous administration. Another problem with exogenously delivered Man-1-P is that its high polarity prevents Man-1-P from penetrating into the cell interior (i.e., cytosol) and thus treating the deficiency in PMM production.

Derivatives of the polar Man-1-P can be synthesized to make Man-1-P more cell-permeable (US Patent Publication No. 2009/0054353). This approach, however, is also problematic, as the cell-permeable Man-1-P derivative has been shown to be either unstable for clinical use or cytotoxic via the by-products of the Man-1-P derivative (Eklund et al., *Glycobiology* 2005, 15: 1084-1093; Rutschow et al. *Bioorg Med Chem* 2002, 10: 4043-4049; and Hardre et at, *Bioorg Med Chem Lett* 2007, 17: 152-155).

Other potential therapies have focused on inhibiting enzymes that catabolize mannose-6-phosphate (Man-6-P), a precursor to Man-1-P, via inhibition of phosphomannose isomerases (PMI). The approach focuses on forcing the reaction towards optimizing homeostasis, which with the use of PMI inhibitors, would have been skewed toward production of Man-6-P. These approaches, however, are ineffective as clinical treatment options due to their associated toxicity, off-target side effects, and poor selective tissue penetration.

Accordingly, unmet needs exist for improved compositions and methods for delivering carbohydrates, such as Man-1-P, to the cell interior in order to treat disorders, such as a congenital disorder of glycosylation (CDG), to subjects (including, for example, humans) in need of such treatment.

BRIEF SUMMARY

The present disclosure meets the unmet needs described above by providing carbohydrates encapsulated by nanocarriers that address the cytotoxicity and stability problems associated with either permeabilizing cells or using carbohydrate derivatives. Such carbohydrates may be endogenous carbohydrates, including, for example, mannose-1-phosphate. By utilizing endocytotic pathways, nanocarriers can enter the cell interior and deliver the carbohydrate into the cytosol of a cell. This implementation of nanocarriers encapsulating carbohydrates, facilitates simultaneously the ease of therapy, allowing for higher dosages of the carbohydrate to reach the biochemical glycosylation pathway, as well as potential easement on administration. In some aspects, the disclosure provides methods for preparation of carbohydrates and glycolipids using nanocarriers for pharmaceutical delivery to cell interior, endoplasmic reticulum, and Golgi. The disclosure provides carbohydrate replacement therapies for, but not limited to, treating diseases of CDG type I and II.

The present disclosure also addresses unmet needs related to effective therapeutics for diseases, such as diseases of CDG, as well as issues related to the delivery of such therapeutics. In some aspects, the disclosure provides a method of delivering carbohydrates such as mannose-1-phosphate to the cytosol of cells. Without wishing to be bound by any theory, it is believed that such method of deliver the carbohydrates (e.g., as part of a medicament) would bypass the work of genetically defective cytosolic enzymes, namely phosphomannomutase (PMM) and phosphomannose isomerase (PMI), which are found prevalent in CDG I disorders.

In some embodiments, the compositions of the present disclosure may involve the delivery of, for example, mannose-1-phosphate into the cytosol of the cell using nanocarriers. In particular, biodegradable and biocompatible lipid-sterol-water lamellar nanostructures may be used to encapsulate the carbohydrate. The disclosed medicament represents the most potent and viable treatment option for disorders, such as the CDG Ia disorder.

In certain embodiments, the present disclosure provides compositions containing a lipid particle and carbohydrates, such as endogenous carbohydrates, encapsulated in the lipid particle, and methods of using such compositions to deliver the carbohydrate to the interior of cells and to treat diseases and disorders, such as congenital disorders of glycosylation (CDG).

In some embodiments, the compositions described herein are medicaments. Such compositions (e.g., medicaments) may include an aqueous suspension of liposomes encasing, for example, mannose-1-phosphate. Liposomes may be prepared from vesicle-forming lipids, such as but not limited to phosphatidylcholine (PC). The liposome may also be prepared in conjunction with a sterol, namely cholesterol. The full liposome may be enriched with polyethylene-glycol (PEG), or PEGylated, in order to enhance circulation and retention with the body fluids upon administration, as well as protect the liposome from premature degradation and excretion of the medicament from the body of a subject in need of such treatment.

Accordingly, certain aspects of the present disclosure relate to a composition comprising a lipid particle; and an endogenous carbohydrate encapsulated in the lipid particle, where the lipid particle contains a molecule that is capable of minimizing degradation of the lipid particle and/or enhancing retention of the lipid particle when administered to a subject, and/or makes the lipid particle immunotolerant when administered to a subject. In some embodiments, the molecule is a stealth molecule, such as ethylene oxide, an ethylene oxide oligomer, an ethylene oxide polymer, polyethylene glycol (PEG), or any combination thereof; and/or a PEGylated neutral lipid.

Other aspects of the present disclosure relate to a composition containing a lipid particle that contains ethylene oxide, an ethylene oxide oligomer, an ethylene oxide polymer, polyethylene glycol (PEG), or any combination thereof; and a carbohydrate encapsulated in the lipid particle. Other aspects of the present disclosure relate to a composition containing a lipid particle; and a carbohydrate encapsulated in the lipid particle, wherein the lipid particle contains choline, ethanolamine, glycerol, inositol, or any combination thereof. In some embodiments, the lipid particle further includes a molecule, such as a stealth molecule, that is capable of minimizing degradation of the lipid particle and/or enhancing retention of the lipid particle when administered to a subject, and/or makes the lipid particle immunotolerant when administered to a subject. In some embodiments, the lipid particle is selected from a liposome, a micelle, a solid lipid nanoparticle, and a niosome. In some embodiments, the lipid particle is a liposome. In some embodiments, the liposome is a stealth liposome that may be immunotolerant. In some embodiments, the endogenous carbohydrate and/or carbohydrate is selected from a monosaccharide, a phosphorylated monosaccharide, a disaccharide, a phosphorylated disaccharide, an oligosaccharide, a phosphorylated oligosaccharide, a polysaccharide, a phosphorylated polysaccharide, mannose, a phosphorylated mannose, a mannofuranose, a phosphorylated mannofuranose, a mannopyranos, a phosphorylated mannopyranos, mannose-1-phosphate, a nucleotide sugar, a uridine diphosphate, a guanine diphosphate, a cytosine monophosphate, fucose, GDP-fucose, a sialic acid, CMP-sialic acid, N-acetylneuraminic acid (Neu5Ac), CMP-Neu5Ac, and derivatives thereof. In some embodiments, the endogenous carbohydrate is mannose-1-phosphate.

Other aspects of the present disclosure relate to a composition containing a liposome; and mannose-1-phosphate encapsulated in the liposome, wherein the liposome comprises cholesterol and phosphatidylethanolamine (PE) attached to polyethylene glycol (PEG).

Other aspects of the present disclosure relate to a pharmaceutical composition containing a composition of any of the preceding embodiments, and a pharmaceutically acceptable carrier.

Other aspects of the present disclosure relate to a kit containing a composition of any of the preceding embodiments for use in any of the methods described herein.

Other aspects of the present disclosure relate to a method for delivering a carbohydrate to a subject in need thereof, by administering to the subject a composition of any of the preceding embodiments. In some embodiments, the composition is administered orally, topically, dermally, nasally, intravenously, intramuscularly, intraperitoneally, intracerobrospinally, intracranially, intraspinally, subcutaneously, intraarticularly, intrasynovialy, or intrathecaly.

Other aspects of the present disclosure relate to a method for delivering a carbohydrate to a cell interior of a subject in need thereof, by administering to the subject a composition of any of the preceding embodiments. In some embodiments, the composition is administered orally, topically, dermally, nasally, intravenously, intramuscularly, intraperitoneally, intracerobrospinally, intracranially, intraspinally, subcutaneously, intra-articularly, intrasynovialy, or intrathecaly.

Other aspects of the present disclosure relate to a method for treating a congenital disorder of glycosylation (CDG) in a subject in need thereof, by administering to the subject a composition of any of the preceding embodiments. In some embodiments, the congenital disorder of glycosylation (CDG) is selected from a CDG type I disorder, a CDG-Ia disorder, a CDG type II disorder, a CDG-IIc disorder, and a CDG-IIf disorder. In some embodiments, the congenital disorder of glycosylation (CDG) is a CDG-Ia disorder. In some embodiments, the composition is administered orally, topically, dermally, nasally, intravenously, intramuscularly, intraperitoneally, intracerobrospinally, intracranially, intraspinally, subcutaneously, intra-articularly, intrasynovialy, or intrathecaly.

DESCRIPTION OF THE DRAWINGS

The following enumerated embodiments are representative of some aspects of the invention.

DETAILED DESCRIPTION

Figure 1A:
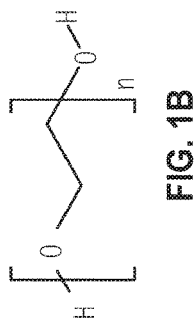
FIG. 1A depicts an exemplary structure of mannose-1-phosphate (M1P).

Provided herein are pharmaceutical nanocarriers of carbohydrates and glycolipids (e.g., lipid compositions containing a lipid particle and one or more carbohydrates) that are capable of delivering the carbohydrates and/or glycolipids to a cell interior including, without limitation, the cytoplasm, endoplasmic reticulum, and Golgi. Suitable nanocarriers include, but are not limited to, liposomes, micelles, solid lipid nanoparticles, and niosomes.

As disclosed herein, the composition of suitable nanocarriers is not limited to any class and molecular weight of lipids, polyethylene glycol, or their derivatives. In some embodiments, the present disclosure relates more specifically, but is not limited to, liposomal preparations of mannose-1-phosphate, guanosine 5'-diphospho-beta-L-fucose (GDP-fucose), cytidine-5'-monophospho-N-acetylneuraminic acid (CMP-sialic acid), and dolichol pyrophosphate linked oligosaccharide, Glc3Man9GlcNAc2-PP-Dol, where Glc=glucose, Man=mannose, GlcNAc=N-Acetylglucosamine, P=phosphate, Dol=dolichol. In some variations, the dolichol may have chain lengths of at least 10 isoprene units, and in certain variations, 14-18 isoprene units.

As disclosed herein in some embodiments, carbohydrates and glycolipids of the present disclosure can be integrated into liposomes designed for specific targeting to cell interior, ER, or Golgi. A chemoenzymatic approach to synthesis of dolichol pyrophosphate linked oligosaccharide may be utilized (Wang Z. et al., *Science*, 2013, 341, 379-383 and Weerapana E. et al., *J. Am. Chem. Soc.*, 2005, 127, 13766-13767). In some embodiments, liposomal preparations may be optimized for each targeted cell compartment as described in Torchilin V. et al., *Curr. Protein Pept. Sci.*, 2003, 4, 133-140; Pollock S. et al., *FASEB*, 2010, 24, 1866-1878; Fujiwara T. et al., *Int. J. Pharm.*, 2010, 386, 122-130; and WO 2009/118658 A2.

In other embodiments, architectural modification to a liposome may include, but not limited to, cholesteryl hemisuccinate (CH) and polyethylene glycol (PEG) chains. As disclosed herein, such modifications can shield carbohydrate and glycolipid moieties of the customized nanoparticle from degradation and will enhance circulation and/or retention time of the pharmaceutical within the body.

Accordingly, the present disclosure provides lipid compositions containing a lipid particle and one or more carbohydrates, such as endogenous carbohydrates, encapsulated in the lipid particle, where the lipid compositions are capable of delivering the carbohydrate into the interior of a cell. In some embodiments, such carbohydrate-carrying lipid compositions are useful for treating, preventing, or reducing risk of a congenital disorder of glycosylation (CDG) in a subject in need thereof. In some embodiments, the lipid particle may be a liposome, a micelle, a solid lipid nanoparticle, or a noisome. In some embodiments, the one or more carbohydrates may be mannose-1-phosphate, guanosine 5'-diphospho-beta-L-fucose (GDP-fucose), and/or cytidine-5'-monophospho-N-acetylneuraminic acid (CMP-sialic acid). In some embodiments, the lipid particle contains a molecule that is capable of minimizing degradation of the lipid particle and/or enhancing retention of the lipid particle when administered to a subject, and/or makes the lipid particle immunotolerant when administered to a subject. As disclosed herein, such molecules may shield, or otherwise protect, the lipid particle and encapsulated carbohydrate of the present disclosure from degradation, and may also enhance cell permeability, circulation and/or retention time of the lipid particle when the lipid particle is administered to a subject in need thereof. Additionally, such molecules can allow the lipid particle to avoid detection by the immune system of a subject in need thereof that is administered the lipid particle, and as such are considered stealth molecules. Accordingly, in some embodiments, the molecule is a stealth molecule that is capable of inducing immunotolerance when administered to a subject in need thereof. Examples of such suitable molecules include, without limitation, ethylene oxide, an ethylene oxide oligomer, an ethylene oxide polymer, polyethylene glycol (PEG), or any combination thereof; and/or a PEGylated neutral lipid.

Thus, in certain aspects, the present disclosure provides a composition containing a lipid particle; and an endogenous carbohydrate encapsulated in the lipid particle, where the lipid particle contains a molecule that is capable of minimizing degradation of the lipid particle and/or enhancing retention of the lipid particle when administered to a subject, and/or makes the lipid particle immunotolerant when administered to a subject. In some embodiments the molecule is a stealth molecule, such as ethylene oxide, an ethylene oxide oligomer, an ethylene oxide polymer, polyethylene glycol (PEG), or any combination thereof; and/or a PEGylated neutral lipid.

In certain aspects, the present disclosure provides a composition containing a lipid particle comprising ethylene oxide, an ethylene oxide oligomer, an ethylene oxide polymer, polyethylene glycol (PEG), or any combination thereof; and a carbohydrate encapsulated in the lipid particle.

In certain aspects, the present disclosure provides a composition containing a lipid particle; and a carbohydrate encapsulated in the lipid particle, wherein the lipid particle comprises choline, ethanolamine, glycerol, inositol, or any combination thereof. In some embodiments, the lipid particle contains a molecule that is capable of minimizing degradation of the lipid particle and/or enhancing retention of the lipid particle when administered to a subject, and/or makes the lipid particle immunotolerant when administered to a subject. In some embodiments the molecule is a stealth molecule, such as ethylene oxide, an ethylene oxide oligomer, an ethylene oxide polymer, polyethylene glycol (PEG), or any combination thereof; and/or a PEGylated neutral lipid.

In certain aspects, the present disclosure provides a composition containing a liposome; and mannose-1-phosphate encapsulated in the liposome, wherein the liposome comprises cholesterol and phosphatidylethanolamine (PE) attached to polyethylene glycol (PEG).

Additionally, pharmaceutical compositions are provided containing a carbohydrate-containing lipid composition of the present disclosure in combination with pharmaceutically acceptable carriers. The present disclosure also provides a kit containing a carbohydrate-containing lipid composition of the present disclosure for use in any of the methods described herein.

The present disclosure further provides methods of using a carbohydrate-containing lipid composition of the present disclosure to deliver a carbohydrate to a subject in need thereof. The present disclosure further provides methods of using a carbohydrate-containing lipid composition of the present disclosure to deliver a carbohydrate to a cell interior to a subject in need thereof. The present disclosure further provides methods of using a carbohydrate-containing lipid composition of the present disclosure to treat, prevent, or reduce risk of a congenital disorder of glycosylation (CDG) in a subject in need thereof.

Lipid Particles

Certain aspects of the present disclosure relate to compositions containing lipid particles that contain carbohydrates encapsulated within the lipid particle.

As used herein, the term "lipid particle" refers to particles formed by lipids in an aqueous solution. Suitable examples of lipid particles include, without limitation, liposomes, micelles, solid lipid nanoparticles, niosome, lipospheres, emulsomes, and emulsions.

As used herein, a carbohydrate that is "encapsulated" in a lipid particle, refers to a lipid particle that provides an active agent or therapeutic agent, such as a carbohydrate of the present disclosure, with full encapsulation, partial encapsulation, or both. In some variations, at least a portion of the carbohydrate may be "encapsulated" by a lipid particle and localized within the core of a lipid particle and/or within the inner surface (e.g., the membrane) of a lipid particle. Alternatively, in other variations, the entire carbohydrate may be "encapsulated" by a lipid particle and localized within the core of a lipid particle and/or within the inner surface (e.g., the membrane) of a lipid particle.

Any lipid particle known in the art suitable for delivering an encapsulated carbohydrate of the present disclosure to the interior of a cell may be used. Examples of suitable lipid particles include, without limitation, liposomes, micelles, solid lipid nanoparticles, and niosomes.

In some embodiments, lipid particles of the present disclosure have an average particle size that ranges from about 0.02 microns in diameter to about 0.5 microns in diameter. In certain embodiments, lipid particles of the present disclosure have an average particle size of about 0.02 microns in diameter, about 0.03 microns in diameter, about 0.04 microns in diameter, about 0.05 microns in diameter, about 0.06 microns in diameter, about 0.07 microns in diameter, about 0.08 microns in diameter, about 0.09 microns in diameter, about 0.10 microns in diameter, about 0.15 microns in diameter, about 0.20 microns in diameter, about 0.25 microns in diameter, about 0.30 microns in diameter, about 0.35 microns in diameter, about 0.40 microns in diameter, about 0.45 microns in diameter, or about 0.50 microns in diameter.

In some embodiments, lipid particles of the present disclosure are capable of delivering a carbohydrate of the present disclosure to the interior of a cell, such as the cytoplasm, endoplasmic reticulum, or Golgi.

In some embodiments, lipid particles of the present disclosure may be optimized for targeting to particular organelles within a cell, including without limitation, the endoplasmic reticulum (ER), Golgi, and lysosome. In some embodiments, lipid particles of the present disclosure may be optimized for targeting to particular tissues and/or organs in a subject. Methods of optimizing lipid particles for targeting specific organelles, tissues, and organs are well known in the art (e.g., Torchilin V et al., *Curr. Protein Pept. Sci.*, 2003, 4, 133-140; Torchilin V et al., *J. Drug Target.*, 2011, 19, 606-614; Huwyler J. et al., *J. Pharmacol. Exp. Ther.*, 1997, 282: 1541-1546; Pollock S. et al., *FASEB*, 2010, 24, 1866-1878; Fujiwara T. et al., *Int. J. Pharm.*, 2010, 386, 122-130; and WO 2009/118658).

In some embodiments, lipid particles of the present disclosure contain a carbohydrate of the present disclosure, that when delivered to the interior of a cell of a subject (including, for example, a human) in need thereof can induce at least a 0.05-fold to at least a 10-fold increase in cellular production of higher-order lipid-linked oligosaccharides, as compared to cellular production of higher-order lipid-linked oligosaccharides in the absence of lipid particles of the present disclosure containing a carbohydrate of the present disclosure. In some embodiments, the lipid particles provided herein, when administered to a subject (including, for example, a human) in need thereof, may induce at least a 0.05-fold, at least a 0.1-fold, at least a 0.2-fold, at least a 0.3-fold, at least a 0.4-fold, at least a 0.5-fold, at least a 0.6-fold, at least a 0.7-fold, at least a 0.8-fold, at least a 0.9-fold, at least a 1-fold, at least a 1.5-fold, at least a 2-fold, at least a 2.5-fold, at least a 3-fold, at least a 3.5-fold, at least a 4-fold, at least a 4.5-fold, at least a 5-fold, at least a 5.5-fold, at least a 6-fold, at least a 6.5-fold, at least a 7-fold, at least a 7.5-fold, at least an 8-fold, at least an 8.5-fold, at least a 9-fold, at least a 9.5-fold, or at least a 10-fold increase in cellular production of higher-order lipid-linked oligosaccharides in the subject, as compared to cellular production of higher-order lipid-linked oligosaccharides in the subject in the absence of administering such lipid particles to the subject.

As used herein a "higher-order lipid-linked oligosaccharide" refers to an oligosaccharide having at least five monosaccharide subunits and that is linked to a lipid. For example, a higher-order linked oligosaccharide may refer to an oligosaccharide containing at least five mannose subunits (Man5), six mannose subunits (Man6), seven mannose subunits (Man7), eight mannose subunits (Man8), or nine mannose subunits (Man9) and an N-acetylglucosamine disaccharide (GlcNAc2), where the oligosaccharide is linked to a dolichol. In some embodiments, the higher-order lipid linked oligosaccharides may include an oligosaccharide portion that includes Man5GlcNAc2, Man6GlcNAc2, Man7GlcNAc2, Man8GlcNAc2, Man8GlcNAc2, or any combination thereof.

Liposomes

In some embodiments, a lipid particle of the present disclosure may be a liposome. As used herein, a "liposome" refers to a vesicle composed of a lamellar phase lipid bilayer. Any suitable liposome known in the art may be used. In some embodiments, the liposome has a lamellar nanostructure. As used herein, the term "lamellar nanostructure" refers to a nanostructure, such as a lipid particle, that includes parallel amphiphilic bilayers separated by a lumen.

Liposomes of the present disclosure may be prepared by any suitable method known in the art and disclosed herein. Examples of suitable methods for preparing liposomes include, without limitation, disrupting biological membranes, such as by mechanical dispersion including sonication, thin-film hydration, emulsions, french pressure cell, extrusion, and reconstitution of dried vesicles; solvent dispersion including ethanol injection, ether injection, double emulsion, reverse phase, and vaporization; and detergent removal methods.

In certain embodiments, the liposome is a stealth liposome that may be immunotolerant. As used herein, the term "stealth liposome" refers to liposomes that are capable of avoiding detection by a subject's immune system. As such, a stealth liposome may be immunotolerant. For example, the subject may be a human.

Micelles

In some embodiments, a lipid particle of the present disclosure may be a micelle. As used herein, a "micelle" refers to an aggregate of surfactant molecules (e.g., soaps, detergents, fatty acids, lipids, phospholipids, etc.) that are dispersed in a liquid colloid. A micelle in aqueous solution may form an aggregate with hydrophilic head regions in contact with surrounding solvent, sequestering the hydrophobic tail regions in the interior of the micelle. Any suitable micelle known in the art may be used. In some embodiments, micelles may be spherical. Micelles of the present disclosure may be prepared by any suitable method known in the art. Examples of suitable methods for preparing micelles include, without limitation, direct dissolution, and direct or microemulsification dialysis, which may encompass preparation by detergent or water-miscible solvent removal methods.

Solid Lipid Nanoparticles

In some embodiments, a lipid particle of the present disclosure may be a solid lipid nanoparticle. As used herein, a "solid lipid nanoparticle" (SLN) refers to lipid in water emulsions composed of lipids that are generally solid at temperatures of at least 50° C., and typically contain a solid lipid core matrix that can solubilize lipophilic molecules. In some variations, solid lipid nanoparticles have a diameter in the range of 10 to 1000 nanometers. Solid lipid nanoparticles may protect incorporated active compounds, such as carbohydrates of the present disclosure, against chemical degradation and can also demonstrate flexibility in modulating the release of such compounds. The lipid core of solid lipid nanoparticles may be stabilized by surfactants (e.g., emulsifiers). The lipid may typically include triglycerides, diglycerides, monoglycerides, fatty acids, steroids, and/or waxes. Any suitable solid lipid nanoparticle known in the art may be used. Solid lipid nanoparticles of the present disclosure may be prepared by any suitable method known in the art. Examples of suitable methods for preparing solid lipid nanoparticles include, without limitation, microemulsification, high-pressure homogenization, precipitation, and film ultrasound dispersion.

Niosomes

In some embodiments, a lipid particle of the present disclosure may be a niosome. As used herein, a "niosome" refers to a vesicular structure formed of a bilayer of non-ionic surfactant molecules and that contains an aqueous core. Niosomes are structurally similar to liposomes in having a lamellar structure, however, the materials used to prepare niosomes make them more stable against hydrolytic degradation. Examples of suitable noisome preparation materials include, without limitation, sterols and one or more non-ionic surfactants. Any suitable niosome known in the art may be used. Niosomes of the present disclosure may be prepared by any suitable method known in the art. Examples of suitable methods for preparing micelles include, without limitation, ether injection, agitation, bubble method, reverse phase evaporation, sonication, multiple membrane extrusion, and microfluidigation.

Components of the Lipid Particles

Lipid particles of the present disclosure (e.g., liposomes, micelles, solid lipid nanoparticles, and niosomes) contain one or more lipids. As used herein, the term "lipid" refers to a substance of biological or synthetic origin that is soluble or partially soluble in organic solvents or which partitions into a hydrophobic environment when present in aqueous phase. In some variations, lipids may be divided into at least three classes: (1) "simple lipids," which include, without limitation, fats, oils, and waxes; (2) "compound lipids," which include, without limitation, phospholipids and glycolipids; and (3) "derived lipids," which include, without limitation, steroids.

In some variations, the lipid may be a neutral lipid or an amphiphilic lipid. As used herein, the term "neutral lipid" refers to a lipid that exists either in an uncharged or neutral zwitterionic form at a selected pH. At physiological pH, such lipids may include, for example, diacylphosphatidylcholine, diacylphosphatidylethanolamine, ceramide, sphingomyelin, cephalin, cholesterol, cerebrosides, and diacylglycerols. As used herein, the term "amphiphilic lipid" refers to a lipid that contains both polar, water-soluble groups and non-polar, water-insoluble groups.

Examples of suitable lipids include, without limitation, bilayer-forming lipids, non-bilayer-forming lipids, amphiphilic lipids, naturally-occurring lipids, phospholipids, glycerolipids, sphingolipids, phosphatidylglycerol, phosphatidic acid, lyso-lipids, fatty acids, sphingomyelin, glycosphingolipids, glucolipids, glycolipids, sulphatides, lipids with ether-linked and ester-linked fatty acids, polymerizable lipids, synthetic lipids, and semi-synthetic lipids. Synthetic or semi-synthetic lipids may be produced via deacylation or reacylation of natural lipids. Suitable features of synthetic and semi-synthetic lipids include, without limitation, myristoyl, palmitoyl, and stearoyl fatty acids. In some embodiments, lipid particles of the present disclosure may contain a mixture of two or more types of lipids. Such mixture may be present at any ratio that is suitable for encapsulating a carbohydrate of the present disclosure and delivering such carbohydrate to a cell interior. In some embodiments, lipid particles of the present disclosure may contain a lipid selected from phospholipid, a glycerolipid, a sphingolipid, and any combination thereof. As disclosed herein, such a lipid has a polar head group and a fatty acid tail that may be linked by, for example, an ester linkage or an ether linkage.

In some embodiments, lipid particles of the present disclosure (e.g., liposomes, micelles, solid lipid nanoparticles, and niosomes) may contain one or more lipids having polar head groups. The lipids may contain any suitable polar head group known in the art. Examples of suitable polar head groups include, without limitation, choline, ethanolamine, serine, glycerol, inositol, and any combination thereof.

In some embodiments, lipid particles of the present disclosure (e.g., liposomes, micelles, solid lipid nanoparticles, and niosomes) may be, without limitation, lamellar nanostructures that contain an amphiphilic lipid. Examples of suitable amphiphilic lipids include, without limitation, phospholipids, cholesterol, glycolipids, fatty acids, bile acids, saponins, and surfactants.

In some embodiments, lipid particles of the present disclosure (e.g., liposomes, micelles, solid lipid nanoparticles, and niosomes) may contain one or more phospholipids. Lipid particles of the present disclosure may contain any suitable phospholipid known in the art. Examples of suitable phospholipids include, without limitation, phosphatidylcholine (PC), phosphatidylethanolamine (PE), phosphatidylserine (PS), phosphatidylglycerol (PG), phosphatidylinositol (PI), and any combination thereof. In some embodiments, lipid particles of the present disclosure may contain phosphatidylcholine (PC). In some embodiments, lipid particles of the present disclosure may contain phosphatidylethanolamine (PE). In certain embodiments, lipid particles of the present disclosure may contain phosphatidylcholine (PC) and phosphatidylethanolamine (PE).

In some embodiments, a phospholipid species of the present disclosure may be present in a lipid particle of the present disclosure (e.g., liposomes, micelles, solid lipid nanoparticles, and niosomes) at a concentration of up to 80 molar percent. In certain embodiments, a phospholipid of the present disclosure may be present in a lipid particle of the present disclosure at a concentration of up to 5 molar percent, up to 10 molar percent, up to 20 molar percent, up to 30 molar percent, up to 40 molar percent, up to 50 molar percent, up to 60 molar percent, up to 70 molar percent, or up to 80 molar percent. In certain embodiments, a phospholipid of the present disclosure may be present in a lipid particle of the present disclosure at a concentration of about 70 molar percent.

In some embodiments, a lipid particle of the present disclosure (e.g., liposomes, micelles, solid lipid nanoparticles, and niosomes) may be modified to, for example, include a molecule, such as a stealth molecule, that shields, or otherwise protects, an encapsulated carbohydrate of the present disclosure from degradation, and that enhances cell permeability, circulation, and/or retention time of the carbohydrate-containing lipid composition within a cell, tissue, organ and/or body of a subject that is administered the carbohydrate-containing lipid composition. Without wishing to be bound by theory, a lipid particle of the present disclosure dramatically enhances cell permeability of carbohydrates, which are otherwise incapable of traversing the plasma membrane. Accordingly, in some embodiments, a lipid particle of the present disclosure includes a molecule that is capable of minimizing degradation of the lipid particle and/or enhancing retention of the lipid particle when administered to a subject, and/or makes the lipid particle immunotolerant when administered to a subject. In some embodiments, the molecule is one or more of ethylene oxide, an ethylene oxide oligomer, an ethylene oxide polymer, polyethylene glycol (PEG), or any combination thereof; and/or a PEGylated neutral lipid. As used herein, the term "PEGylated neutral lipid" refers to a neutral lipid, at a selected pH, to which a polyethylene glycol has been conjugated.

As used herein, the terms "ethylene oxide," "oxirane," "epoxyethane," "dimethylene oxide," and "oxacyclopropane" may be used interchangeably and refer to a cyclic ether having the formula $C_2H_4O$.

As used herein, the terms "polyethylene glycol," "PEG," "polyethylene oxide," "PEO," "polyoxyethylene," and "POE" may be used interchangeably and refer to a polyether compound that is composed of two or more ethylene oxide subunits. "Polyethylene glycol" may be composed of ethylene oxide oligomers (e.g., having from two to nine ethylene oxide monomer subunits) or ethylene oxide polymers (e.g., having ten or more nine ethylene oxide monomer subunits).

In some embodiments, a lipid particle of the present disclosure may be modified to include one or more lipids conjugated to polyethylene glycol (PEG) in order to allow the lipid particle to avoid detection by the immune system of a subject that is administered the lipid particle. In some embodiments, a lipid particle of the present disclosure (e.g., liposomes, micelles, solid lipid nanoparticles, and niosomes) increases cell permeability for hydrophobic carbohydrates, such as endogenous carbohydrates of the present disclosure, that are otherwise unable to get through the cell membrane on their own.

Accordingly, in some embodiments, lipid particles of the present disclosure (e.g., liposomes, micelles, solid lipid nanoparticles, and niosomes) contain ethylene oxide, oligomers of ethylene oxide and/or polymers of ethylene oxide. In certain embodiments, lipid particles of the present disclosure contain polyethylene glycol (PEG). Alternatively, in some embodiments, lipid particles of the present disclosure (e.g., liposomes, micelles, solid lipid nanoparticles, and niosomes) may contain, without limitation, polyvinyl pyrrolidone (PVP), polyacryl amide (PAA), $G_{M1}$ ganglioside, cerebroside, and/or sulfates. Without wishing to be bound by theory, such modifications can shield lipid particles from opsonization.

In some embodiments, polyethylene glycol (PEG) may be present in a lipid particle of the present disclosure (e.g., liposomes, micelles, solid lipid nanoparticles, and niosomes) at a concentration that ranges from about 0.5 molar percent to about 20 molar percent. In some embodiments, PEG may be present in a lipid particle of the present disclosure (e.g., liposomes, micelles, solid lipid nanoparticles, and niosomes) at a concentration of about 0.5 molar percent, about 1 molar percent, about 2 molar percent, about 3 molar percent, about 4 molar percent, about 5 molar percent, about 6 molar percent, about 7 molar percent, about 8 molar percent, about 9 molar percent, about 10 molar percent, about 11 molar percent, about 12 molar percent, about 13 molar percent, about 14 molar percent, about 15 molar percent, about 16 molar percent, about 17 molar percent, about 18 molar percent, about 19 molar percent, or about 20 molar percent.

In some embodiments, polyethylene glycol (PEG) may be present in a lipid particle of the present disclosure (e.g., liposomes, micelles, solid lipid nanoparticles, and niosomes) at a molecular weight concentration that ranges from about 200 Da to about 10,000 Da. In some embodiments, polyethylene glycol (PEG) may be present in a lipid particle of the present disclosure (e.g., liposomes, micelles, solid lipid nanoparticles, and niosomes) at a molecular weight concentration of about 200 Da, about 300 Da, about 400 Da, about 500 Da, about 600 Da, about 700 Da, about 800 Da, about 900 Da, about 1,000 Da, about 1,500 Da, about 2,000 Da, about 2,500 Da, about 3,000 Da, about 3,500 Da, about 4,000 Da, about 4,500 Da, about 5,000 Da, about 5,500 Da, about 6,000 Da, about 6,500 Da, about 7,000 Da, about 7,500 Da, about 8,000 Da, about 8,500 Da, about 9,000 Da, about 9,500 Da, or about 10,000 Da.

In some embodiments, lipid particles of the present disclosure (e.g., liposomes, micelles, solid lipid nanoparticles, and niosomes) may contain PEG conjugated to a phospholipid of the present disclosure. The PEG may be conjugated to one or more of phosphatidylcholine (PC), phosphatidylethanolamine (PE), phosphatidylserine (PS), phosphatidylglycerol (PG), phosphatidylinositol (PI), and any combination thereof. In certain embodiments, lipid particles of the present disclosure may contain PEG conjugated to phosphatidylcholine (PC). In certain embodiments, lipid particles of the present disclosure may contain PEG conjugated to phosphatidylethanolamine (PE).

In some embodiments, a phospholipid conjugated to polyethylene glycol (PEG) may be present in a lipid particle of the present disclosure (e.g., liposomes, micelles, solid lipid nanoparticles, and niosomes) at a concentration that ranges from about 0.5 molar percent to about 20 molar percent. In some embodiments, a phospholipid conjugated to polyethylene glycol (PEG) may be present in a lipid particle of the present disclosure (e.g., liposomes, micelles, solid lipid nanoparticles, and niosomes) at a concentration of about 0.5 molar percent, about 1 molar percent, about 2 molar percent, about 3 molar percent, about 4 molar percent, about 5 molar percent, about 6 molar percent, about 7 molar percent, about 8 molar percent, about 9 molar percent, about 10 molar percent, about 11 molar percent, about 12 molar percent, about 13 molar percent, about 14 molar percent, about 15 molar percent, about 16 molar percent, about 17 molar percent, about 18 molar percent, about 19 molar percent, or about 20 molar percent. In certain embodiments, a phospholipid conjugated to polyethylene glycol (PEG) may be present in a lipid particle of the present disclosure at a concentration of about 2 molar percent.

In some embodiments, lipid particles of the present disclosure (e.g., liposomes, micelles, solid lipid nanoparticles, and niosomes) may contain one or more sterols. Examples of suitable phospholipids include, without limitation, cholesterol and cholesteryl hemisuccinate (CH), dicetyl phosphate, and Solulan C24.

In some embodiments, a sterol of the present disclosure, such as cholesterol, may be present in a lipid particle of the present disclosure (e.g., liposomes, micelles, solid lipid nanoparticles, and niosomes) at a concentration of up to 40 molar percent. In some embodiments, a sterol of the present disclosure, such as cholesterol, may be present in a lipid particle of the present disclosure (e.g., liposomes, micelles, solid lipid nanoparticles, and niosomes) at a concentration of up to 5 molar percent, up to 10 molar percent, up to 15 molar percent, up to 20 molar percent, up to 30 molar percent, or up to 40 molar percent. In certain embodiments, a sterol of the present disclosure, such as cholesterol, may be present in a lipid particle of the present disclosure at a concentration of at most 15 molar percent. In some embodiments, a sterol of the present disclosure, such as cholesterol, may be present in a lipid particle of the present disclosure (e.g., liposomes, micelles, solid lipid nanoparticles, and niosomes) at a molar ratio of 1:1 or 2:1.

In some embodiments, lipid particles of the present disclosure (e.g., liposomes, micelles, solid lipid nanoparticles, and niosomes) may contain one or more fatty acids. In some embodiments, fatty acids of the present disclosure may have a carbon chain that ranges in length from about 14 carbon atoms to about 18 carbon atoms.

In some embodiments, lipid particles of the present disclosure (e.g., liposomes, micelles, solid lipid nanoparticles, and niosomes) may contain one or more neutral lipids. In certain embodiments, a neutral lipid of the present disclosure may be PEGylated (i.e., conjugated to PEG). In some embodiments, a PEGylated neutral lipid of the present disclosure may be present in a lipid particle of the present disclosure at a concentration that ranges from about 0.2 molar percent to about 20 molar percent. In some embodiments, a neutral lipid of the present disclosure may be PEGylated (i.e., conjugated to PEG). In some embodiments, a PEGylated neutral lipid of the present disclosure may be present in a lipid particle of the present disclosure at a concentration of about 0.5 molar percent, about 1 molar percent, about 2 molar percent, about 3 molar percent, about 4 molar percent, about 5 molar percent, about 6 molar percent, about 7 molar percent, about 8 molar percent, about 9 molar percent, about 10 molar percent, about 11 molar percent, about 12 molar percent, about 13 molar percent, about 14 molar percent, about 15 molar percent, about 16 molar percent, about 17 molar percent, about 18 molar percent, about 19 molar percent, or about 20 molar percent.

In some embodiments, lipid particles of the present disclosure (e.g., liposomes, micelles, solid lipid nanoparticles, and niosomes) may be modified to target specific organelles and/or tissues. Any suitable method known in the art may be used to target a lipid particle to an organelle and/or tissue. Suitable examples include, without limitation, modification of the material used for the preparation of the lipid particle itself (e.g., by utilizing distinct mixtures and molar ratios of phospholipids such as PC, PS, PI, and PE), covalent attachment of a linker (e.g., peptide chains such as poly-arginine chains and octadecyl-rhodamine B) to the lipid particle surface, or an antibody modification. For example, octadecyl-rhodamine B modification can target a lipid particle to the lysosome of cells. In some embodiments, lipid particles of the present disclosure (e.g., liposomes, micelles, solid lipid nanoparticles, and niosomes) may be antibody-conjugated liposomes, or immunoliposomes, that may be used to direct encapsulated carbohydrates of the present disclosure to diseased tissues and/or organs.

Carbohydrates

Other aspects of the present disclosure relate to compositions containing carbohydrates encapsulated within a lipid particle of the present disclosure (e.g., liposomes, micelles, solid lipid nanoparticles, and niosomes). Any suitable carbohydrate known in the art may be used. Examples of suitable carbohydrates that may be used include, without limitation, monosaccharides, phosphorylated monosaccharides, disaccharides, phosphorylated disaccharides, oligosaccharides, phosphorylated oligosaccharides, polysaccharides, phosphorylated polysaccharides, nucleotide sugars, endogenous carbohydrates, and phosphorylated endogenous carbohydrates.

In some embodiments, the carbohydrate may be present within a lipid particle of the present disclosure at a concentration that ranges from about 0.10 mg per mL of lipid particle to about 10 mg per mL of lipid particle. In some embodiments, the carbohydrate may be present within a lipid particle of the present disclosure at a concentration of about 0.10 mg per mL of lipid particle, about 0.20 mg per mL of lipid particle, about 0.30 mg per mL of lipid particle, about 0.40 mg per mL of lipid particle, about 0.50 mg per mL of lipid particle, about 0.60 mg per mL of lipid particle, about 0.70 mg per mL of lipid particle, about 0.80 mg per mL of lipid particle, about 0.90 mg per mL of lipid particle, about 1 mg per mL of lipid particle, about 1.50 mg per mL of lipid particle, about 2 mg per mL of lipid particle, about 2.50 mg per mL of lipid particle, about 3 mg per mL of lipid particle, about 3.50 mg per mL of lipid particle, about 4 mg per mL of lipid particle, about 4.50 mg per mL of lipid particle, about 5 mg per mL of lipid particle, 5.50 mg per mL of lipid particle, about 6 mg per mL of lipid particle, 6.50 mg per mL of lipid particle, about 7 mg per mL of lipid particle, 7.50 mg per mL of lipid particle, about 8 mg per mL of lipid particle, 8.50 mg per mL of lipid particle, about 9 mg per mL of lipid particle, about 9.50 mg per mL of lipid particle, or about 10 mg per mL of lipid particle. In certain embodiments, a carbohydrate of the present disclosure may be present within a lipid particle of the present disclosure at a concentration of about 1 mg per mL of lipid particle.

In some embodiments, a carbohydrate of the present disclosure is an endogenous carbohydrate. As used herein, "endogenous carbohydrate" refers to a carbohydrate that is found as a natural product in a subject (including, for example, a human). It should be understood, however, that an endogenous carbohydrate may be either (i) naturally produced by a subject (including, for example, a human) and extracted from the living cells of such subject, or (ii) synthetically made. In some embodiments, the endogenous carbohydrate is produced in vivo by a subject (including, for example, human). In other embodiments, the endogenous carbohydrate is naturally produced by a cell derived from a subject (including, for example, human), such as a cultured cell line. Thus, the source of such endogenous carbohydrates may include, without limitation, a synthetic source (e.g., chemical synthesis) or a natural source (e.g., extraction, isolation, or purification from a subject or cell that naturally produces the endogenous carbohydrate or a recombinant cell, such as a bacterial cell, that has been genetically engineered to produce the endogenous carbohydrate). Examples of endogenous carbohydrates may include, without limitation, carbohydrates involved in protein and lipid glycosylation.

Examples of suitable endogenous carbohydrates include, without limitation, a monosaccharide, a phosphorylated monosaccharide, a disaccharide, a phosphorylated disaccharide, an oligosaccharide, a phosphorylated oligosaccharide, a polysaccharide, a phosphorylated polysaccharide, mannose, a phosphorylated mannose, a mannofuranose, a phosphorylated mannofuranose, a mannopyranos, a phosphorylated mannopyranos, mannose-1-phosphate, a nucleotide sugar, a uridine diphosphate, a guanine diphosphate, a cytosine monophosphate, fucose, GDP-fucose, a sialic acid, CMP-sialic acid, N-acetylneuraminic acid (NeuSAc), and CMP-Neu5Ac.

In other embodiments, the carbohydrate is a dolichol pyrophosphate linked oligosaccharide, Glc3Man9GlcNAc2-PP-Dol, where Glc=glucose, Man=mannose, GlcNAc=N-Acetylglucosamine, P=phosphate, and Dol=dolichol with a chain length that includes, but not limited to, 14-18 isoprene units. Any suitable method known in the art for preparing dolichol pyrophosphate linked oligosaccharides may be used. In one example, a chemoenzymatic approach may be used to synthesize dolichol pyrophosphate linked oligosaccharide (e.g., Wang Z. et al., Science, 2013, 341, 379-383 and Weerapana E. et al., J. Am. Chem. Soc., 2005, 127, 13766-13767).

Other aspects of the present disclosure relate to compositions containing glycolipids encapsulated within a lipid particle of the present disclosure. Any suitable glycolipid known in the art may be used. Glycolipids of the present disclosure include, without limitation, any class and molecular weight of lipids and carbohydrates.

In some embodiments, carbohydrates and glycolipids of the present disclosure may be integrated into lipid particles of the present disclosure, such as liposomes, that may be designed for specific targeting to a cell interior, the ER of a cell, or the Golgi of a cell.

Pharmaceutical Compositions

Compositions of the present disclosure containing a lipid particle of the present disclosure and a carbohydrate of the present disclosure encapsulated in the lipid particle can be incorporated into a variety of formulations for therapeutic use (e.g., by administration) or in the manufacture of a medicament (e.g., for delivering a carbohydrate of the present disclosure to a subject in need thereof and/or cell interior of a subject in need thereof and/or for treating or preventing a disease or disorder such as a congenital disorder of glycosylation (CDG) in a subject in need thereof) by combining the composition with appropriate carriers (including, for example, pharmaceutically acceptable carriers or diluents), and may be formulated, without limitation, into preparations in liquid, aerosolized, semisolid, or powder forms.

"Carriers" as used herein include pharmaceutically acceptable carriers, excipients, or stabilizers that are non-toxic to the cell or subject being exposed thereto at the dosages and concentrations employed. Often the physiologically acceptable carrier is an aqueous pH buffered solution. Examples of physiologically acceptable carriers include, without limitation, buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Examples of suitable formulations include, without limitation, solutions, injections, inhalants, microspheres, aerosols, gels, ointments, creams, lotions, powders, dry vesicular powders, tablets, and capsules. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include, without limitation, other carriers or non-toxic, non-therapeutic, nonimmunogenic stabilizers, and excipients. The compositions can also include additional substances to approximate physiological conditions, such as pH adjusting and buffering agents, toxicity adjusting agents, wetting agents and detergents. A pharmaceutical composition of the present disclosure can also include any of a variety of stabilizing agents, such as an antioxidant for example.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Pharmaceutical Dosages

Pharmaceutical compositions of the present disclosure containing a composition containing a lipid particle of the present disclosure and a carbohydrate of the present disclosure encapsulated by the lipid particle may be used (e.g., administered to a subject in need of treatment with a carbohydrate of the present disclosure, such as a human individual) in accord with known methods, such as oral administration, intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the compositions of the present disclosure containing a lipid particle of the present disclosure and a carbohydrate of the present disclosure encapsulated by the lipid particle, normal dosage amounts may vary from 10 ng/kg up to 100 mg/kg of a subject's body weight per day.

Administration of a composition of the present disclosure containing a lipid particle of the present disclosure and a carbohydrate of the present disclosure encapsulated by the lipid particle can be continuous or intermittent, depending, for example, on the recipient's physiological condition, whether the purpose of the administration is therapeutic or prophylactic, and other factors known to skilled practitioners.

It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Thus, in some variations, the compositions provided herein may be chronically or intermittently administered to a subject (including, for example, a human) in need thereof. "Chronic" administration refers to administration of the medicament(s) in a continuous as opposed to acute mode, so as to maintain the initial therapeutic effect (activity) for an extended period of time. "Intermittent" administration refers to treatment that is not consecutively done without interruption, but rather is cyclic in nature.

Therapeutic Uses

The present disclosure provides compositions containing a lipid particle of the present disclosure and a carbohydrate of the present disclosure encapsulated by the lipid particle that are capable of delivering the carbohydrate into the interior of a cell. These compositions are useful for delivering carbohydrates of the present disclosure to a subject in need of such carbohydrates.

As used herein, the term "subject" refers to a mammal, such as a human, domestic animal, such as a feline or canine subject, farm animal (e.g., bovine, equine, caprine, ovine, and porcine subject), wild animal (whether in the wild or in a zoological garden), research animal, such as mouse, rat, rabbit, goat, sheep, pig, dog, and cat, and birds. In one embodiment, the subject is a human.

In some variations, the subject may be at risk. For example, in one variation, the subject is an at risk human. As used herein, a subject "at risk" of developing a particular disease, disorder, or condition, such as a congenital disorder of glycosylation, may or may not have detectable disease or symptoms of disease, and may or may not have displayed detectable disease or symptoms of disease prior to the treatment methods described herein. "At risk" denotes that an individual has risk factors, which are measurable parameters that correlate with development of a particular disease, disorder, or condition, as known in the art. A subject having one or more of these risk factors has a higher probability of developing a particular disease, disorder, or condition such as a congenital disorder of glycosylation, than a subject without one or more of these risk factors.

In some embodiments, compositions containing a lipid particle of the present disclosure and a carbohydrate of the present disclosure encapsulated by the lipid particle may also be used for delivering carbohydrates of the present disclosure to the cell interior of a subject in need thereof. In certain embodiments, compositions containing a lipid particle of the present disclosure and a carbohydrate of the present disclosure encapsulated by the lipid particle may be used for preventing, reducing risk, or treating a disease or disorder, such as a congenital disorder of glycosylation (CDG) in a subject in need thereof.

Accordingly, as disclosed herein, compositions of the present disclosure containing a lipid particle of the present disclosure and a carbohydrate of the present disclosure encapsulated by the lipid particle may be used for delivering a carbohydrate of the present disclosure to a subject in need thereof, for delivering a carbohydrate of the present disclosure to the cell interior of a subject in need thereof, and for treating, preventing, or reducing risk of a disease or disorder, such as a congenital disorder of glycosylation (CDG) in a subject in need thereof. In some embodiments, the subject has such a disease or disorder. In some embodiments, the subject is a human having such a disease or disorder.

As used herein, the term "congenital disorders of glycosylation" (CDG) refers to a group of genetic disorders that result in errors of metabolism in which glycosylation of a variety of tissue proteins and/or lipids is deficient or defective. Congenital disorders of glycosylation may also be known as CDG syndromes. CDG syndromes may often cause serious, occasionally fatal, malfunction of several different organ systems, such as the nervous system, brain, muscles, and intestines, in affected infants. Manifestations of CDG syndromes may range from severe developmental delay and hypotonia beginning in infancy, to hypoglycemia and protein-losing enteropathy with normal development. Developmental delay can be a common initial indication for a CDG diagnosis. One of the most common subtype of CDG syndromes is CDG-Ia (also known as PMM2-CDG) where the genetic defect leads to the loss of phosphomannomutase 2, which is the enzyme responsible for the conversion of mannose-6-phosphate into mannose-1-phosphate.

CDG syndromes may be classified as type I (CDG-I) and type II (CDG-II). Such classification may depend on the nature and location of the biochemical defect in the metabolic pathway relative to the action of oligosaccharyltransferase. Methods for screening for CDG subtype may include the analysis of transferrin glycosylation status by, for example, isoelectric focusing or ESI-MS. Examples of CDG type I include, without limitation, Ia (PMM2-CDG), Ib (MPI-CDG), Ic (ALG6-CDG), Id (ALG3-CDG), Ie (DPM1-CDG), If (MPDU1-CDG), Ig (ALG12-CDG), Ih (ALG8-CDG), Ii (ALG2-CDG), Ij (DPAGT1-CDG), Ik (ALG1-CDG), 1 L (ALG9-CDG), Im (DOLK-CDG), In (RFT1-CDG), Io (DPM3-CDG), Ip (ALG11-CDG), Iq (SRD5A3-CDG), Ir (DDOST-CDG), DPM2-CDG, TUSC3-CDG, MAGT1-CDG, DHDDS-CDG, and I/IIx. Examples of CDG type II include, without limitation, IIa (MGAT2-CDG), IIb (GCS1-CDG), IIc (SLC335C1-CDG), IId (B4GALT1-CDG), IIe (COG7-CDG), IIf (SLC35A1-CDG), IIg (COG1-CDG), IIh (COG8-CDG), IIi (COG5-CDG), IIj (COG4-CDG), IIL (COG6-CDG), ATP6V0A2-CDG, MAN1B1-CDG, and ST3GAL3-CDG.

Congenital disorders of glycosylation (CDG) that may be treated with compositions of the present disclosure containing a lipid particle of the present disclosure and a carbohydrate of the present disclosure encapsulated by the lipid particle include, without limitation, Ia (PMM2-CDG), Ib (MPI-CDG), Ic (ALG6-CDG), Id (ALG3-CDG), Ie (DPM1-CDG), If (MPDU1-CDG), Ig (ALG12-CDG), Ih (ALG8-CDG), Ii (ALG2-CDG), Ij (DPAGT1-CDG), Ik (ALG1-CDG), 1 L (ALG9-CDG), Im (DOLK-CDG), In (RFT1-CDG), Jo (DPM3-CDG), Ip (ALG11-CDG), Iq (SRD5A3-CDG), Ir (DDOST-CDG), DPM2-CDG, TUSC3-CDG, MAGT1-CDG, DHDDS-CDG, I/IIx, IIa (MGAT2-CDG), IIb (GCS1-CDG), IIc (SLC335C1-CDG), IId (B4GALT1-CDG), IIe (COG7-CDG), IIf (SLC35A1-CDG), IIg (COG1-CDG), IIh (COG8-CDG), IIi (COG5-CDG), IIj (COG4-CDG), IIL (COG6-CDG), ATP6V0A2-CDG, MAN1B1-CDG, and ST3GAL3-CDG.

Accordingly, the compositions of the present disclosure containing a lipid particle of the present disclosure and a carbohydrate of the present disclosure encapsulated by the lipid particle may be used to treat, prevent, or improve one or more symptoms of a congenital disorder of glycosylation (CDG) of the present disclosure. In some embodiments, the present disclosure provides methods of treating, preventing, or improving one or more symptoms in subjects having a congenital disorder of glycosylation (CDG) disorder of the present disclosure by administering to the subject a composition of the present disclosure containing a lipid particle of the present disclosure and a carbohydrate of the present disclosure encapsulated by the lipid particle to, for example, deliver a carbohydrate to the subject to correct, or otherwise improve protein and/or lipid glycosylation in the subject.

In some embodiments, the present disclosure provides methods for treating, preventing, or improving one or more symptoms of a congenital disorder of glycosylation (CDG) to a subject in need thereof, by administering to the subject a therapeutically effective amount of a composition comprising a lipid particle; and an endogenous carbohydrate encapsulated in the lipid particle. In some embodiments, the present disclosure provides methods for treating, preventing, or improving one or more symptoms of a congenital disorder of glycosylation (CDG) to a subject in need thereof, by administering to the subject a therapeutically effective amount of a composition comprising a lipid particle comprising ethylene oxide; and a carbohydrate encapsulated in the lipid particle. In some embodiments, the present disclosure provides methods for treating, preventing, or improving one or more symptoms of a congenital disorder of glycosylation (CDG) to a subject in need thereof, by administering to the subject a therapeutically effective amount of a composition comprising a lipid particle; and a carbohydrate encapsulated in the lipid particle, wherein the lipid particle comprises choline, ethanolamine, glycerol, inositol, or any combination thereof. In some embodiments, the present disclosure provides methods for treating, preventing, or improving one or more symptoms of a congenital disorder of glycosylation (CDG) to a subject in need thereof, by administering to the subject a therapeutically effective amount of a composition comprising a liposome; and mannose-1-phosphate encapsulated in the liposome, wherein the liposome comprises cholesterol and phosphatidylethanolamine (PE) attached to polyethylene glycol (PEG). In some embodiments, the congenital disorder of glycosylation (CDG) may be a CDG type I disorder, a CDG-Ia disorder, a CDG type II disorder, a CDG-IIc disorder, or a CDG-IIf disorder. In certain embodiments, the congenital disorder of glycosylation (CDG) is a CDG-Ia disorder. In some embodiments, the composition is administered orally, dermally, nasally, or intravenously.

As used herein, the term "treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

As used herein, the term "prevention" or "preventing" refers to any treatment of a disease or condition that causes the clinical symptoms of the disease or condition not to develop. Compounds may, in some embodiments, be administered to a subject (including a human) who is at risk or has a family history of the disease or condition.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease, disorder, or condition, such as a congenital disorder of glycosylation. A therapeutically effective amount herein may vary according to factors such as the disease state, age, sex, and weight of the subject, and the ability of the lipid compositions of the present disclosure to elicit a desired response in the subject. A therapeutically effective amount is also one in which any toxic or detrimental effects of the lipid compositions of the present disclosure are outweighed by the therapeutically beneficial effects.

In other aspects of the present disclosure, compositions of the present disclosure containing a lipid particle of the present disclosure and a carbohydrate of the present disclosure encapsulated by the lipid particle may be used for delivering a carbohydrate to a subject in need thereof. Accordingly, in some embodiments, the present disclosure provides methods for delivering a carbohydrate to a subject in need thereof, by administering to the subject a therapeutically effective amount of a composition comprising a lipid particle; and an endogenous carbohydrate encapsulated in the lipid particle. In some embodiments, the present disclosure provides methods for delivering a carbohydrate to a subject in need thereof, by administering to the subject a therapeutically effective amount of a composition comprising a lipid particle comprising ethylene oxide; and a carbohydrate encapsulated in the lipid particle. In some embodiments, the present disclosure provides methods for delivering a carbohydrate to a subject in need thereof, by administering to the subject a therapeutically effective amount of a composition comprising a lipid particle; and a carbohydrate encapsulated in the lipid particle, wherein the lipid particle comprises choline, ethanolamine, glycerol, inositol, or any combination thereof. In some embodiments, the present disclosure provides methods for delivering a carbohydrate to a subject in need thereof, by administering to the subject a therapeutically effective amount of a composition comprising a liposome; and mannose-1-phosphate encapsulated in the liposome, wherein the liposome comprises cholesterol and phosphatidylethanolamine (PE) attached to polyethylene glycol (PEG). In some embodiments, the subject has a congenital disorder of glycosylation (CDG). In some embodiments, the congenital disorder of glycosylation (CDG) may be a CDG type I disorder, a CDG-Ia disorder, a CDG type II disorder, a CDG-IIc disorder, and a CDG-IIf disorder. In certain embodiments, the congenital disorder of glycosylation (CDG) is a CDG-Ia disorder.

In other aspects of the present disclosure, compositions of the present disclosure containing a lipid particle of the present disclosure and a carbohydrate of the present disclosure encapsulated by the lipid particle may be used for delivering a carbohydrate to a cell interior of a subject in need thereof. Accordingly, in some embodiments, the present disclosure provides methods for delivering a carbohydrate to a cell interior of a subject in need thereof, by administering to the subject a therapeutically effective amount of a composition comprising a lipid particle; and an endogenous carbohydrate encapsulated in the lipid particle, wherein the administered composition traverses the cell plasma membrane thereby delivering the carbohydrate to the cell interior. In some embodiments, the present disclosure provides methods for delivering a carbohydrate to a cell interior of a subject in need thereof, by administering to the subject a therapeutically effective amount of a composition comprising a lipid particle comprising ethylene oxide; and a carbohydrate encapsulated in the lipid particle, wherein the administered composition traverses the cell plasma membrane thereby delivering the carbohydrate to the cell interior. In some embodiments, the present disclosure provides methods for delivering a carbohydrate to a cell interior of a subject in need thereof, by administering to the subject a therapeutically effective amount of a composition comprising a lipid particle; and a carbohydrate encapsulated in the lipid particle, wherein the lipid particle comprises choline, ethanolamine, glycerol, inositol, or any combination thereof, and wherein the administered composition traverses the cell plasma membrane thereby delivering the carbohydrate to the cell interior. In some embodiments, the present disclosure provides methods for delivering a carbohydrate to a cell interior of a subject in need thereof, by administering to the subject a therapeutically effective amount of a composition comprising a liposome; and mannose-1-phosphate encapsulated in the liposome, wherein the liposome comprises cholesterol and phosphatidylethanolamine (PE) attached to polyethylene glycol (PEG), and wherein the administered composition traverses the cell plasma membrane thereby delivering the carbohydrate to the cell interior. In some embodiments, the subject has a congenital disorder of glycosylation (CDG). In some embodiments, the congenital disorder of glycosylation (CDG) may be a CDG type I disorder, a CDG-Ia disorder, a CDG type II disorder, a CDG-IIc disorder, and a CDG-IIf disorder. In certain embodiments, the congenital disorder of glycosylation (CDG) is a CDG-Ia disorder. In some embodiments, administration of the composition induces at least a 0.05-fold to at least a 3-fold increase in cellular production of higher-order lipid-linked oligosaccharides in the subject, as compared to cellular production of higher-order lipid-linked oligosaccharides in the subject in the absence of the composition. In certain embodiments, the higher-order lipid-linked oligosaccharides comprise Man5GlcNAc2, Man6GlcNAc2, Man7GlcNAc2, Man8GlcNAc2, Man9GlcNAc2, or any combination thereof. In some embodiments, the composition is administered orally, topically, dermally, nasally, intravenously, intramuscularly, intraperitoneally, intracerebrospinally, intracranially, intraspinally, subcutaneously, intraarticularly, intrasynovialy, or intrathecaly.

Articles of Manufacture and Kits

The present disclosure also provides articles of manufacture and/or kits containing a composition of the present disclosure containing a lipid particle of the present disclosure and a carbohydrate of the present disclosure encapsulated by the lipid particle. Articles of manufacture and/or kits of the present disclosure may include one or more containers comprising a purified composition of the present disclosure. Suitable containers may include, without limitation, bottles, vials, syringes, and IV solution bags. The containers may be formed from a variety of materials such as glass or plastic. In some embodiments, the articles of manufacture and/or kits further include instructions for use in accordance with any of the methods of the present disclosure. In some embodiments, these instructions comprise a description of administration of the composition containing a lipid particle of the present disclosure and a carbohydrate of the present disclosure encapsulated by the lipid particle to deliver the carbohydrate to a subject in need thereof, to deliver the carbohydrate to a cell interior of a subject in need thereof, or to treat a congenital disorder of glycosylation (CDG) to a subject in need thereof, according to any of the methods of the present disclosure. In some embodiments, the instructions comprise a description of how to detect a congenital disorder of glycosylation (CDG), for example in a subject, in a tissue sample, or in a cell. The article of manufacture and/or kit may further comprise a description of selecting a subject suitable for treatment based on identifying whether that subject has the disease and the stage of the disease.

The instructions generally include information as to dosage, dosing schedule, and route of administration for the intended treatment. The containers may be unit doses, bulk packages (e.g., multi-dose packages) or sub-unit doses. Instructions supplied in the articles of manufacture and/or kits of the present disclosure are typically written instructions on a label or package insert (e.g., a paper sheet included in the article of manufacture and/or kit), but machine-readable instructions (e.g., instructions carried on a magnetic or optical storage disk) are also acceptable.

The label or package insert indicates that the composition is used for delivering a carbohydrate and/or treating, e.g., a congenital disorder of glycosylation (CDG). Instructions may be provided for practicing any of the methods described herein.

The articles of manufacture and/or kits of the present disclosure may be in suitable packaging. Suitable packaging includes, without limitation, vials, bottles, jars, and flexible packaging (e.g., sealed Mylar or plastic bags). Also contemplated are packages for use in combination with a specific device, such as an inhaler, nasal administration device (e.g., an atomizer) or an infusion device such as a minipump. An article of manufacture and/or kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is a carbohydrate capable of treating a congenital disorder of glycosylation (CDG) and/or improving one or more symptoms thereof. The container may further comprise a second pharmaceutically active agent.

Articles of manufacture and/or kits may optionally provide additional components such as buffers and interpretive information. Normally, the article of manufacture and/or kit comprises a container and a label or package insert(s) on or associated with the container.

Unless defined otherwise, all scientific and technical terms are understood to have the same meaning as commonly used in the art to which they pertain. For the purpose of the present disclosure, the following terms are defined.

The term "about" as used herein refers to the usual error range for the respective value readily known to the skilled person in this technical field. Reference to "about" a value or parameter herein includes (and describes) embodiments that are directed to that value or parameter per se. For example, "about x" includes and describes "x" per se. In some embodiments, the term "about" when used in association with a measurement, or used to modify a value, a unit, a constant, or a range of values, refers to variations of +/−2%.

As used herein and in the appended claims, the singular forms "a," "an," and "the" include plural reference unless the context clearly indicates otherwise. For example, reference to a "lipid particle" is a reference to from one to many lipid particles, such as molar amounts, and includes equivalents thereof known to those skilled in the art, and so forth.

ENUMERATED EMBODIMENTS

The following enumerated embodiments are representative of some aspects of the invention.
1. A composition comprising:
   a lipid particle; and
   an endogenous carbohydrate encapsulated in the lipid particle.
2. The composition of embodiment 1, wherein the lipid particle comprises a molecule that is capable of minimizing degradation of the lipid particle and/or enhancing retention of the lipid particle when administered to a subject, and/or makes the lipid particle immunotolerant when administered to a subject.
3. The composition of embodiment 2, wherein the molecule is ethylene oxide, an ethylene oxide oligomer, an ethylene oxide polymer, polyethylene glycol (PEG), or any combination thereof.
4. The composition of embodiment 2, wherein the molecule is ethylene oxide.
5. The composition of embodiment 2, wherein the molecule is an ethylene oxide oligomer or an ethylene oxide polymer.
6. The composition of embodiment 2, wherein the molecule is polyethylene glycol (PEG).
7. The composition of any one of embodiments 1-6, wherein the lipid particle further comprises a lipid selected from the group consisting of a phospholipid, a glycerolipid, a sphingolipid, and any combination thereof; optionally wherein the lipid comprises choline, ethanolamine, serine, glycerol, inositol, or any combination thereof.
8. The composition of any one of embodiments 1-7, wherein the lipid particle further comprises a lipid having a polar head group.
9. The composition of embodiment 8, wherein the polar head group is selected from the group consisting of choline, ethanolamine, serine, glycerol, inositol, and any combination thereof.
10. The composition of any one of embodiments 1-7, wherein the lipid particle further comprises a phospholipid.
11. The composition of embodiment 10, wherein the phospholipid comprises phosphatidylcholine (PC), phosphatidylethanolamine (PE), phosphatidylserine (PS), phosphatidylglycerol (PG), phosphatidylinositol (PI), or any combination thereof.
12. The composition of any one of embodiments 1-11, wherein the lipid particle further comprises a sterol.
13. The composition of embodiment 12, wherein the sterol is cholesterol.
14. The composition of embodiment 13, wherein the cholesterol is present at a concentration of at most 15 molar percent.

15. The composition of any one of embodiments 1-14, wherein the lipid particle further comprises a fatty acid.
16. The composition of any one of embodiments 1-15, wherein the lipid particle further comprises a PEGylated neutral lipid.
17. The composition of any one of embodiments 1-16, wherein the lipid particle is a lamellar nanostructure comprising an amphiphilic lipid.
18. The composition of any one of embodiments 1-17, wherein the lipid particle is selected from the group consisting of a liposome, a micelle, a solid lipid nanoparticle, and a niosome.
19. The composition of any one of embodiments 1-17, wherein the lipid particle is a liposome.
20. The composition of embodiment 17, wherein the liposome comprises polyethylene-glycol (PEG).
21. The composition of embodiment 20, wherein the liposome is a stealth liposome.
22. The composition of embodiment 21, wherein the stealth liposome is immunotolerant.
23. The composition of any one of embodiments 19-22, wherein the liposome further comprises a phospholipid selected from the group consisting of phosphatidylcholine (PC), phosphatidylethanolamine (PE), phosphatidylserine (PS), phosphatidylglycerol (PG), phosphatidylinositol (PI), and any combination thereof.
24. The composition of any one of embodiments 19-22, wherein the liposome further comprises phosphatidylcholine (PC) and phosphatidylethanolamine (PE).
25. The composition of any one of embodiments 19-24, wherein the liposome further comprises phosphatidylcholine (PC) at a concentration of at least 70 molar percent.
26. The composition of any one of embodiments 19-25, wherein the liposome further comprises a PEGylated neutral lipid.
27. The composition of embodiment 26, wherein the PEGylated neutral lipid is present in the lipid particle at a concentration of at least 1 molar percent.
28. The composition of any one of embodiments 19-27, wherein the liposome further comprises cholesterol.
29. The composition of any one of embodiments 19-28, wherein the liposome further comprises a fatty acid.
30. The composition of embodiment 29, wherein the fatty acid comprises a carbon chain that ranges in length from 14-18 carbon atoms.
31. The composition of any one of embodiments 1-17, wherein the lipid particle is a micelle.
32. The composition of any one of embodiments 1-17, wherein the lipid particle is a solid lipid nanoparticle.
33. The composition of any one of embodiments 1-17, wherein the lipid particle is a niosome.
34. The composition of any one of embodiments 1-33, wherein the endogenous carbohydrate is selected from the group consisting of a monosaccharide, a phosphorylated monosaccharide, a disaccharide, a phosphorylated disaccharide, an oligosaccharide, a phosphorylated oligosaccharide, a polysaccharide, a phosphorylated polysaccharide, mannose, a phosphorylated mannose, a mannofuranose, a phosphorylated mannofuranose, a mannopyranos, a phosphorylated mannopyranos, mannose-1-phosphate, a nucleotide sugar, a uridine diphosphate, a guanine diphosphate, a cytosine monophosphate, fucose, GDP-fucose, a sialic acid, CMP-sialic acid, N-acetylneuraminic acid (Neu5Ac), and CMP-Neu5Ac.
35. The composition of any one of embodiments 1-33, wherein the endogenous carbohydrate is mannose-1-phosphate.
36. The composition of any one of embodiments 1-33, wherein the endogenous carbohydrate is GDP-fucose.
37. The composition of any one of embodiments 1-33, wherein the endogenous carbohydrate is CMP-sialic acid.
38. The composition of any one of embodiments 1-37, wherein the lipid particle has an average particle size that ranges from 0.05 to 0.5 microns in diameter.
39. The composition of any one of embodiments 1-38, wherein the lipid particle is capable of delivering the endogenous carbohydrate to a cell interior.
40. The composition of any one of embodiments 1-39, wherein the composition when administered to a subject in need thereof induces at least a 0.05-fold to at least a 3-fold increase in cellular production of higher-order lipid-linked oligosaccharides in the subject, as compared to cellular production of higher-order lipid-linked oligosaccharides in the subject in the absence of administering the composition to the subject.
41. The composition of embodiment 40, wherein the higher-order lipid-linked oligosaccharides comprise Man5GlcNAc2, Man6GlcNAc2, Man7GlcNAc2, Man8GlcNAc2, Man9GlcNAc2, or any combination thereof.
42. A composition comprising:
a lipid particle comprising ethylene oxide, an ethylene oxide oligomer, an ethylene oxide polymer, polyethylene glycol (PEG), or any combination thereof; and
a carbohydrate encapsulated in the lipid particle.
43. The composition of embodiment 42, wherein the carbohydrate is an endogenous carbohydrate.
44. The composition of embodiment 43, wherein the endogenous carbohydrate is selected from the group consisting of a monosaccharide, a phosphorylated monosaccharide, a disaccharide, a phosphorylated disaccharide, an oligosaccharide, a phosphorylated oligosaccharide, a polysaccharide, a phosphorylated polysaccharide, mannose, a phosphorylated mannose, a mannofuranose, a phosphorylated mannofuranose, a mannopyranos, a phosphorylated mannopyranos, mannose-1-phosphate, a nucleotide sugar, a uridine diphosphate, a guanine diphosphate, a cytosine monophosphate, fucose, GDP-fucose, a sialic acid, CMP-sialic acid, N-acetylneuraminic acid (Neu5Ac), and CMP-Neu5Ac.
45. The composition of embodiment 42, wherein the carbohydrate is mannose-1-phosphate.
46. The composition of embodiment 42, wherein the carbohydrate is GDP-fucose.
47. The composition of embodiment 42, wherein the carbohydrate is CMP-sialic acid.
48. The composition of any one of embodiments 42-47, wherein the lipid particle comprises an ethylene oxide oligomer.
49. The composition of any one of embodiments 42-47, wherein the lipid particle comprises an ethylene oxide polymer.
50. The composition of any one of embodiments 42-47, wherein the lipid particle comprises polyethylene glycol (PEG).
51. The composition of any one of embodiments 42-50, wherein the lipid particle further comprises choline, ethanolamine, serine, glycerol, inositol, or any combination thereof.
52. The composition of any one of embodiments 42-51, wherein the lipid particle further comprises a lipid selected from the group consisting of a phospholipid, a glycerolipid, a sphingolipid, and any combination thereof.

53. The composition of embodiment 52, wherein the lipid comprises a polar head group.
54. The composition of embodiment 53, wherein the polar head group is selected from the group consisting of choline, ethanolamine, serine, glycerol, inositol, and any combination thereof.
55. The composition of any one of embodiments 42-52, wherein the lipid particle further comprises a phospholipid.
56. The composition of embodiment 55, wherein the phospholipid is selected from the group consisting of phosphatidylcholine (PC), phosphatidylethanolamine (PE), phosphatidylserine (PS), phosphatidylglycerol (PG), phosphatidylinositol (PI), and any combination thereof.
57. The composition of any one of embodiments 42-56, wherein the lipid particle further comprises a sterol.
58. The composition of embodiment 57, wherein the sterol is cholesterol.
59. The composition of embodiment 58, wherein the cholesterol is present at a concentration of at most 15 molar percent.
60. The composition of any one of embodiments 42-59, wherein the lipid particle further comprises a fatty acid.
61. The composition of any one of embodiments 42-60, wherein the lipid particle further comprises a PEGylated neutral lipid.
62. The composition of any one of embodiments 42-61, wherein the lipid particle is a lamellar nanostructure comprising an amphiphilic lipid.
63. The composition of any one of embodiments 42-62, wherein the lipid particle is selected from the group consisting of a liposome, a micelle, a solid lipid nanoparticle, and a niosome.
64. The composition of any one of embodiments 42-62, wherein the lipid particle is a liposome.
65. The composition of embodiment 64, wherein the liposome comprises polyethylene-glycol (PEG).
66. The composition of embodiment 65, wherein the liposome is a stealth liposome.
67. The composition of embodiment 66, wherein the stealth liposome is immunotolerant.
68. The composition of any one of embodiments 64-67, wherein the liposome further comprises a phospholipid selected from the group consisting of phosphatidylcholine (PC), phosphatidylethanolamine (PE), phosphatidylserine (PS), phosphatidylglycerol (PG), phosphatidylinositol (PI), and any combination thereof.
69. The composition of any one of embodiments 64-67, wherein the liposome further comprises phosphatidylcholine (PC) and phosphatidylethanolamine (PE).
70. The composition of any one of embodiments 64-69, wherein the liposome comprises phosphatidylcholine (PC) at a concentration of at least 70 molar percent.
71. The composition of any one of embodiments 64-70, wherein the liposome further comprises a PEGylated neutral lipid.
72. The composition of embodiment 71, wherein the PEGylated neutral lipid is present in the lipid particle at a concentration of at least 1 molar percent.
73. The composition of any one of embodiments 64-72, wherein the liposome further comprises cholesterol.
74. The composition of any one of embodiments 64-73, wherein the liposome further comprises a fatty acid.
75. The composition of embodiment 74, wherein the fatty acid comprises a carbon chain that ranges in length from 14-18 carbon atoms.
76. The composition of any one of embodiments 42-62, wherein the lipid particle is a micelle.
77. The composition of any one of embodiments 42-62, wherein the lipid particle is a solid lipid nanoparticle.
78. The composition of any one of embodiments 42-62, wherein the lipid particle is a niosome.
79. The composition of any one of embodiments 42-78, wherein the lipid particle has an average particle size that ranges from 0.05 to 0.5 microns in diameter.
80. The composition of any one of embodiments 42-79, wherein the lipid particle is capable of delivering the carbohydrate to a cell interior.
81. The composition of any one of embodiments 42-80, wherein the composition when administered to a subject induces at least a 0.05-fold to at least a 3-fold increase in cellular production of higher-order lipid-linked oligosaccharides in the subject, as compared to cellular production of higher-order lipid-linked oligosaccharides in the subject in the absence of the composition.
82. The composition of embodiment 81, wherein the higher-order lipid-linked oligosaccharides comprise Man5GlcNAc2, Man6GlcNAc2, Man7GlcNAc2, Man8GlcNAc2, Man9GlcNAc2, or any combination thereof.
83. A composition comprising:
    a lipid particle; and
    a carbohydrate encapsulated in the lipid particle,
    wherein the lipid particle comprises choline, ethanolamine, glycerol, inositol, or any combination thereof.
84. The composition of embodiment 83, wherein the lipid particle further comprises a molecule that is capable of minimizing degradation of the lipid particle and/or enhancing retention of the lipid particle when administered to a subject, and/or makes the lipid particle immunotolerant when administered to a subject.
85. The composition of embodiment 83 or 84, wherein the carbohydrate is an endogenous carbohydrate.
86. The composition of embodiment 85, wherein the endogenous carbohydrate is selected from the group consisting of a monosaccharide, a phosphorylated monosaccharide, a disaccharide, a phosphorylated disaccharide, an oligosaccharide, a phosphorylated oligosaccharide, a polysaccharide, a phosphorylated polysaccharide, mannose, a phosphorylated mannose, a mannofuranose, a phosphorylated mannofuranose, a mannopyranos, a phosphorylated mannopyranos, mannose-1-phosphate, a nucleotide sugar, a uridine diphosphate, a guanine diphosphate, a cytosine monophosphate, fucose, GDP-fucose, a sialic acid, CMP-sialic acid, N-acetylneuraminic acid (NeuSAc), and CMP-Neu5Ac.
87. The composition of embodiment 83 or 84, wherein the carbohydrate is mannose-1-phosphate.
88. The composition of embodiment 83 or 84, wherein the carbohydrate is GDP-fucose.
89. The composition of embodiment 83 or 84, wherein the carbohydrate is CMP-sialic acid.
90. The composition of any one of embodiments 83-89, wherein the lipid particle comprises ethylene oxide, an ethylene oxide oligomer, an ethylene oxide polymer, polyethylene glycol (PEG), or any combination thereof.
91. The composition of embodiment 90, wherein the lipid particle comprises an ethylene oxide oligomer.
92. The composition of embodiment 90, wherein the lipid particle comprises an ethylene oxide polymer.
93. The composition of embodiment 90, wherein the lipid particle comprises polyethylene glycol (PEG).

94. The composition of any one of embodiments 83-93, wherein the lipid particle further comprises a lipid selected from the group consisting of a phospholipid, a glycerolipid, a sphingolipid, and any combination thereof; optionally wherein the lipid has a polar head group.

95. The composition of embodiment 94, wherein the polar head group is selected from the group consisting of choline, ethanolamine, glycerol, inositol, and any combination thereof.

96. The composition of any one of embodiments 83-93, wherein the lipid particle further comprises a phospholipid.

97. The composition of embodiment 96, wherein the phospholipid is selected from the group consisting of phosphatidylcholine (PC), phosphatidylethanolamine (PE), phosphatidylglycerol (PG), phosphatidylinositol (PI), and any combination thereof.

98. The composition of any one of embodiments 83-97, wherein the lipid particle further comprises a sterol.

99. The composition of embodiment 98, wherein the sterol is cholesterol.

100. The composition of embodiment 99, wherein the cholesterol is present at a concentration of at most 15 molar percent.

101. The composition of any one of embodiments 83-100, wherein the lipid particle further comprises a fatty acid.

102. The composition of any one of embodiments 83-101, wherein the lipid particle further comprises a PEGylated neutral lipid.

103. The composition of any one of embodiments 83-102, wherein the lipid particle is a lamellar nanostructure comprising an amphiphilic lipid.

104. The composition of any one of embodiments 83-103, wherein the lipid particle is selected from the group consisting of a liposome, a micelle, a solid lipid nanoparticle, and a niosome.

105. The composition of any one of embodiments 83-103, wherein the lipid particle is a liposome.

106. The composition of embodiment 105, wherein the liposome comprises polyethylene-glycol (PEG).

107. The composition of embodiment 105 or 106, wherein the liposome is a stealth liposome.

108. The composition of embodiment 107, wherein the stealth liposome is immunotolerant.

109. The composition of any one of embodiments 105-108, wherein the liposome further comprises a phospholipid selected from the group consisting of phosphatidylcholine (PC), phosphatidylethanolamine (PE), phosphatidylglycerol (PG), phosphatidylinositol (PI), and any combination thereof.

110. The composition of any one of embodiments 105-108, wherein the liposome further comprises phosphatidylcholine (PC) and phosphatidylethanolamine (PE).

111. The composition of any one of embodiments 105-110, wherein the liposome comprises phosphatidylcholine (PC) at a concentration of at least 70 molar percent.

112. The composition of any one of embodiments 105-111, wherein the liposome further comprises a PEGylated neutral lipid.

113. The composition of embodiment 112, wherein the PEGylated neutral lipid is present in the lipid particle at a concentration of at least 1 molar percent.

114. The composition of any one of embodiments 105-113, wherein the liposome further comprises cholesterol.

115. The composition of any one of embodiments 105-114, wherein the liposome further comprises a fatty acid.

116. The composition of embodiment 115, wherein the fatty acid comprises a carbon chain that ranges in length from 14-18 carbon atoms.

117. The composition of any one of embodiments 83-103, wherein the lipid particle is a micelle.

118. The composition of any one of embodiments 83-103, wherein the lipid particle is a solid lipid nanoparticle.

119. The composition of any one of embodiments 83-103, wherein the lipid particle is a niosome.

120. The composition of any one of embodiments 83-119, wherein the lipid particle has an average particle size that ranges from 0.05 to 0.5 microns in diameter.

121. The composition of any one of embodiments 83-120, wherein the lipid particle is capable of delivering the carbohydrate to a cell interior.

122. The composition of any one of embodiments 83-121, wherein the composition when administered to a subject induces at least a 0.05-fold to at least a 3-fold increase in cellular production of higher-order lipid-linked oligosaccharides in the subject, as compared to cellular production of higher-order lipid-linked oligosaccharides in the subject in the absence of the composition.

123. The composition of embodiment 122, wherein the higher-order lipid-linked oligosaccharides comprise Man5GlcNAc2, Man6GlcNAc2, Man7GlcNAc2, Man8GlcNAc2, Man9GlcNAc2, or any combination thereof.

124. A composition comprising:
 a liposome; and
 mannose-1-phosphate encapsulated in the liposome,
wherein the liposome comprises cholesterol and phosphatidylethanolamine (PE) attached to polyethylene glycol (PEG).

125. The composition of embodiment 124, wherein the liposome is a stealth liposome.

126. The composition of embodiment 125, wherein the stealth liposome is immunotolerant.

127. The composition of any one of embodiments 124-126, wherein the liposome further comprises a phospholipid selected from the group consisting of phosphatidylcholine (PC), phosphatidylserine (PS), phosphatidylglycerol (PG), phosphatidylinositol (PI), and any combination thereof.

128. The composition of any one of embodiments 124-126, wherein the liposome further comprises phosphatidylcholine (PC).

129. The composition of embodiment 127 or 128, wherein the liposome comprises phosphatidylcholine (PC) at a concentration of at least 70 molar percent.

130. The composition of any one of embodiments 124-129, wherein the liposome further comprises a PEGylated neutral lipid.

131. The composition of embodiment 130, wherein the PEGylated neutral lipid is present in the lipid particle at a concentration of at least 1 molar percent.

132. The composition of any one of embodiments 124-131, wherein the cholesterol is present at a concentration of at most 15 molar percent.

133. The composition of any one of embodiments 124-132, wherein the liposome further comprises a fatty acid.

134. The composition of embodiment 133, wherein the fatty acid comprises a carbon chain that ranges in length from 14-18 carbon atoms.

135. The composition of any one of embodiments 124-134, wherein the liposome has an average particle size that ranges from 0.05 to 0.5 microns in diameter.

136. The composition of any one of embodiments 124-135, wherein the 1 liposome is capable of delivering the mannose-1-phosphate to a cell interior.

137. The composition of any one of embodiments 124-136, wherein the composition when administered to a subject induces at least a 0.05-fold to at least a 3-fold increase in cellular production of higher-order lipid-linked oligosaccharides in the subject, as compared to cellular production of higher-order lipid-linked oligosaccharides in the subject in the absence of the composition.

138. The composition of embodiment 137, wherein the higher-order lipid-linked oligosaccharides comprise Man5GlcNAc2, Man6GlcNAc2, Man7GlcNAc2, Man8GlcNAc2, Man9GlcNAc2, or any combination thereof.

139. Use of the composition of any one of embodiments 1-138 in the manufacture of a medicament for delivering a carbohydrate to a subject.

140. Use of the composition of any one of embodiments 1-138 in the manufacture of a medicament for delivering a carbohydrate to a cell interior.

141. Use of the composition of any one of embodiments 1-138 in the manufacture of a medicament for treating a congenital disorder of glycosylation (CDG).

142. The composition of any one of embodiments 1-138 for use in delivering a carbohydrate to a subject in need thereof.

143. The composition of any one of embodiments 1-138 for use in delivering a carbohydrate to a cell interior of a subject in need thereof.

144. The composition of any one of embodiments 1-138 for use in treating a congenital disorder of glycosylation (CDG) to a subject in need thereof.

145. A pharmaceutical composition comprising the composition of any one of embodiments 1-138, and a pharmaceutically acceptable carrier.

146. A kit comprising the composition of any one of embodiments 1-138.

147. The kit of embodiment 146, wherein the kit further comprises a package insert comprising instructions for using the composition to treat a congenital disorder of glycosylation (CDG) in a subject in need of such treatment.

148. The kit of embodiment 146, wherein the kit further comprises a package insert comprising instructions for using the composition to deliver a carbohydrate to a subject in need of such treatment.

149. The kit of embodiment 146, wherein the kit further comprises a package insert comprising instructions for using the composition to deliver a carbohydrate to a cell interior.

150. A method for delivering a carbohydrate to a subject in need thereof, comprising administering to the subject the composition of any one of embodiments 1-138.

151. The method of embodiment 150, wherein the subject has a congenital disorder of glycosylation (CDG).

152. The method of embodiment 151, wherein the congenital disorder of glycosylation (CDG) is selected from the group consisting of a CDG type I disorder, a CDG-Ia disorder, a CDG type II disorder, a CDG-IIc disorder, and a CDG-IIf disorder.

153. The method of embodiment 151, wherein the congenital disorder of glycosylation (CDG) is a CDG-Ia disorder.

154. A method for delivering a carbohydrate to a cell interior of a subject in need thereof, comprising administering to the subject the composition of any one of embodiments 1-138, wherein the administered composition traverses the cell plasma membrane to deliver the carbohydrate to the cell interior.

155. The method of embodiment 154, wherein the subject has a congenital disorder of glycosylation (CDG).

156. The method of embodiment 155, wherein the congenital disorder of glycosylation (CDG) is selected from the group consisting of a CDG type I disorder, a CDG-Ia disorder, a CDG type II disorder, a CDG-IIc disorder, and a CDG-IIf disorder.

157. The method of embodiment 155, wherein the congenital disorder of glycosylation (CDG) is a CDG-Ia disorder.

158. A method for treating a congenital disorder of glycosylation (CDG) in a subject in need thereof, comprising administering to the subject the composition of any one of embodiments 1-138.

159. The method of embodiment 158, wherein the congenital disorder of glycosylation (CDG) is selected from the group consisting of a CDG type I disorder, a CDG-Ia disorder, a CDG type II disorder, a CDG-IIc disorder, and a CDG-IIf disorder.

160. The method of embodiment 158, wherein the congenital disorder of glycosylation (CDG) is a CDG-Ia disorder.

161. The method of any one of embodiments 150-160, wherein administration of the composition induces at least a 0.05-fold to at least a 3-fold increase in cellular production of higher-order lipid-linked oligosaccharides in the subject, as compared to cellular production of higher-order lipid-linked oligosaccharides in the subject in the absence of the composition.

162. The method of embodiment 161, wherein the higher-order lipid-linked oligosaccharides comprise Man5GlcNAc2, Man6GlcNAc2, Man7GlcNAc2, Man8GlcNAc2, Man9GlcNAc2, or any combination thereof.

163. The method of any one of embodiments 150-162, wherein administration of the composition minimizes degradation of the lipid particle and/or enhances retention of the lipid particle when administered to the subject, and/or makes the lipid particle immunotolerant when administered to the subject.

164. The method of any one of embodiments 150-163, wherein the composition is administered orally, topically, dermally, nasally, intravenously, intramuscularly, intraperitoneally, intracerobrospinally, intracranially, intraspinally, subcutaneously, intra-articularly, intrasynovialy, or intrathecaly.

165. Pharmaceutical nanocarriers of dolichol pyrophosphate linked oligosaccharide to endoplasmic reticulum are capable of treating all CDG type I disorders.

166. Pharmaceutical nanocarriers of mannose-1 phosphate to cell interior are capable of treating CDG-Ia disorder.

167. Pharmaceutical nanocarriers of GDP-fucose to Golgi are capable of treating CDG-IIc disorder.

168. Pharmaceutical nanocarriers of CMP-sialic acid to Golgi are capable of treating CDG-IIf disorder.

EXAMPLES

The invention will be more fully understood by reference to the following Examples. They should not, however, be construed as limiting the scope of the invention. All citations throughout the disclosure are hereby expressly incorporated by reference.

Abbreviations

"PC" corresponds to phosphatidylcholine.

"PE" corresponds to phosphatidylethanolamine

"PEG" corresponds to 1,2-distearoyl-sn-glycero-3-phosphoethanolamine-N-[amino(polyethylene glycol)-2000] or just Poly-ethylene-glycol.

"M1P" corresponds to mannose-1-phosphate.

"PBS" corresponds to phosphate buffered saline solution.

"MWCO" corresponds to molecular weight cut-off membrane.

Materials and Methods

Liposomes

Materials for liposome preparation (PC, PE, and PE-PEG) were purchased from Avanti Polar Lipids.

Cell Lines

CDG-Ia human dermal fibroblasts and wild-type human dermal fibroblasts were purchased from Coriell Institute.

Culture Media

Dulbecco's min. Eagle's media was purchased from Mediatech.

Alpha-minimal essential medium was purchased from Mediatech.

Glutamine and penicillin-streptomycin were purchased from Omega Scientific.

FBS was purchased from Thermo.

Example 1

Preparation of Mannose-1-Phosphate Liposomes

The following Example demonstrates the preparation of liposomes containing mannose-1-phosphate (M1P-liposomes). The structure of mannose-1-phosphate (M1P) is depicted in FIG. 1A. While a specific isomer is depicted in FIG. 1A, it should be understood that the carbohydates used in the compositions and methods provided herein may be any isomeric form, provided that such carbohydrates are endogenous carbohydrates for a given subject.

Liposome Preparation Method

Figure 1B:
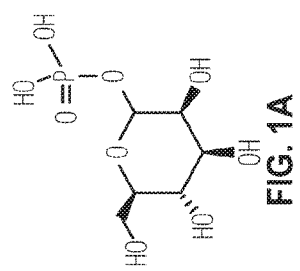
FIG. 1B depicts an exemplary structure of polyethylene glycol (PEG).
Figure 1C:
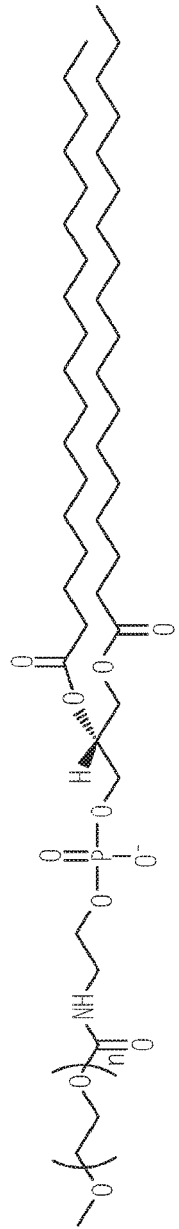
FIG. 1C depicts an exemplary structure of phosphatidylethanolamine (PE) attached to PEG.
Figure 1D:
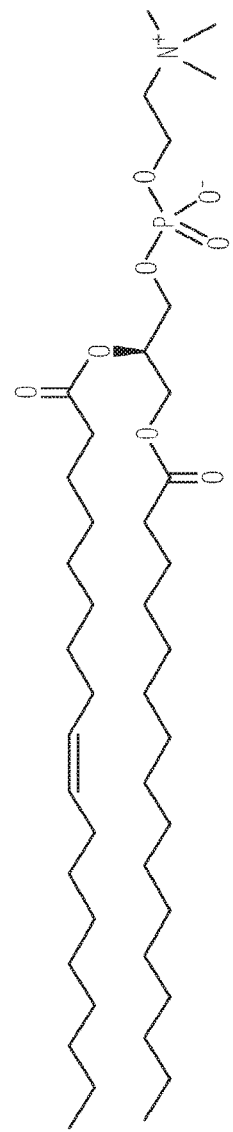
FIG. 1D depicts an exemplary structure of phosphatidylcholine (PC).

Liposomes were prepared by thin-film hydration from phosphatidylcholine (PC), cholesterol, and phosphatidylethanolamine (PE) conjugated topoly-ethylene-glycol (PEG). The structure of PEG is depicted in FIG. 1B. In FIG. 1B, in one variation, n may be in the range of 800-5000. In other variations, the value of n may be 2000. In yet other variations, PEG may be modified either with meleimide or NHS-ester depending on what the PEG will be conjugated to. The structure of phosphatidylethanolamine attached to PEG (PEG-PE) is depicted in FIG. 1C. The structure of phosphatidylcholine (PC) is depicted in FIG. 1D.

The bulk solvent from the lipid film of PC and cholesterol was removed by rotary evaporation for 30 minutes, followed by freeze drying for 4 hours to remove trace amounts of solvent. Following this, the liposomes were rehydrated first with a solution of mannose-1-phosphate (M1P) in 1× phosphate buffered saline pH 7.4 (PBS) at a M1P concentration of 10 mg/mL. Then, PBS was further added so as to achieve a lipid concentration of 20 mg/mL. Liposomes were then heated to 39° C. and sized or extruded through 200 nm pore size and then 100 nm pore size polycarbonate membranes using a mini handheld extruder. Liposomes were then dialyzed against PBS using a 2 kDa molecular weight cut-off membrane (MWCO).

Figure 2:
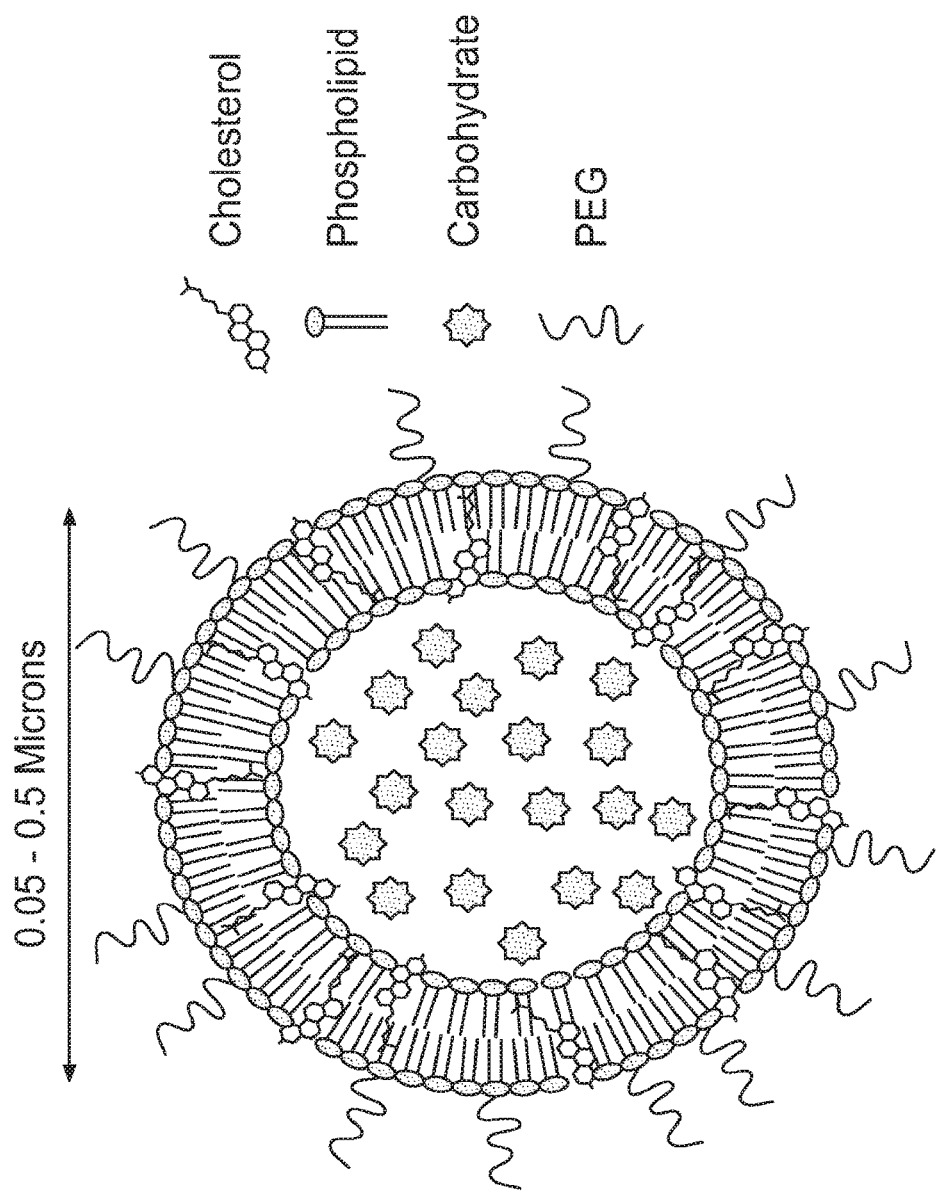
FIG. 2 depicts an exemplary the structure of a liposome composition containing a carbohydrate encapsulated within the core of the liposome.

Following this step, 1,2-distearoyl-sn-glycero-3-phosphoethanolamine-N-[amino(polyethylene glycol)-2000] (PEG) was added by post-insertion. Briefly, a thin film of PEG was obtained by drying off solvent using a stream of $N_2$ gas and freeze drying as mentioned previously. This film was then rehydrated using the prepared M1P-loaded liposomal solution. After vortexing for 5 minutes, the solution was incubated at 37° C. overnight to allow for post-insertion of PEG into the core of the nanoparticle. The structure of the mannose-1-phosphate-loaded liposomes is depicted in FIG. 2.

TABLE 1

| Formulation | Molar percentage (%) | Weight (mg) |
| --- | --- | --- |
| PC | 70 | 16.7 |
| Cholesterol | 30 | 3.64 |
| DSPE-PEG$_{2000}$ | 2 | 1.75 |
| M1P | 5 | 1.0 |

In Table 1, the final volume of the liposome formulation was 1 mL.

Example 2

Measurement of M1P Content in Liposomes

CDG-Ia disorder is a gycosylation disorder characterized by the deficiency or abnormalities associated with the enzyme phosphomannomutase (PMM). This disorder is diagnosed by testing the serum glycoproteins of hepatic origin (transferrin is the clinically tested protein), which are commonly underglycosylated. Typically transferrin is assessed using isoelectric focusing, which would underscore a dramatic decrease in PMM activity (PMM activity in CDG-Ia patients is approximately 0.29 nM/min/mg, as compared to normal PMM activity of approximately 2.97 nM/min/mg). PMM enzyme is responsible for catalyzing the conversion of mannose-6-phosphate to mannose-1-phosphate, which is in turn a precursor for the ultimate synthesis of $G_3M_9Gn_2$-P-P-Dolichol, which in turn is a precursor to lipid-linked-oligosaccharide (LLO). This is represented by the following schematic representation of the metabolic glycosylation pathway is: glucose→glucose-6-phosphate→fructose-6-phosphate →mannose→mannose-6-phosphate→mannose-1-phosphate→GDP-mannose→peptide N-glycosylation.

Typical LLO oligosaccharides include mannose subunits (M) linked to an N-acetylglucosamine disaccharide ($Gn_2$). The decrease in PMM activity thus hampers the full maturation of LLO oligosaccharides, which typically range in size from $M_5Gn_2$ to $M_9Gn_2$. The resulting immature LLO oligosaccharides are not fully functional LLO and are typically truncated. Immature LLO oligosaccharides typically have sizes of $M_2Gn_2$ and $M_3Gn_2$.

Analysis of synthesized oligosaccharide chains is typically performed by incubating fibroblasts with radiolabeled mannose in order to verify any divergence from established patterns of oligosaccharide maturation. This is typically accomplished by labeling newly-synthesized oligosaccharides within the human fibroblasts with [2-$^3$H]mannose. Following incubation with labeled mannose, cell lysates are digested to further analyze the labeled sugars by chromatography. However, a steady supply of mannose is necessary to ensure a continuous production of the saccharide chain. (S. Catherine Hubbard and Phillips W. Robbins. *Journal of Biological Chemistry* (1980) 255: 11782-11793). A problem with the approach of systematically supplying mannose within the body to treat disorders, such as CDG-Ia, is the inability of mannose to traverse the plasma membrane. Hence various mannose derivatives have been evaluated for their ability to accumulate within the cytosol of cells.

However, this approach is also problematic, due to the toxicity and instability of such derivatives.

The following Example demonstrates the capacity of M1P-liposomes to drive the biosynthesis and full maturation of various LLO oligosaccharides. This approach bypasses the need to either permeabilize cells or to use a mannose derivative.

Lipid Sample Preparation

Lipids were precipitated with 10% Triton X-100 using a ratio of 1:1 liposome:detergent, respectively. Lipid precipitate was removed by centrifugation. Isolated M1P was treated with HCl at a final concentration of 0.1 N; 1-phospho linkage was hydrolyzed for 15 min at 100° C. Samples were dried down in a speed vacuum in preparation for labeling with a fluorophore for detection and quantiation as described by Alwael et al. (*Anal. Methods*, 2011, 3, 62). Concentration of M1P in liposomes was 1.0 mg per milliliter of formulation equivalent to 5% of total lipid concentration.

Therapeutic/Trials

Cellular internalization into the cytosol and subsequent integration of the M1P-liposomes (as prepared in Example 1), was assessed in vitro using primary human dermal fibroblasts derived from patients affected with CDG-Ia disorder (CDG-Ia fibroblasts) and wild-type human dermal fibroblasts. For evaluation of the ability of the M1P-liposomes to correct protein glycosylation defects, M1P-liposomes were delivered to CDG Type I primary fibroblasts derived from patients affected with CDG-Ia disorder. The ability to drive glycosylation forward was evaluated by comparing glycoprotein N-glycan structure before and after treatment. Such comparison required N-glycan analysis using normal phase chromatography.

By utilizing endocytotic pathways, M1P-liposomes can enter the cell interior and release their cargo into the cytosol. Due to the ability to deliver a non-modified mannose-1-phosphate into the cytosol, analysis was performed on the assembly of LLO oligosaccharides in wild-type fibroblasts and fibroblasts derived from a CDG-Ia patient (CDG-Ia fibroblasts). LLO structures were isolated from the wild-type fibroblasts (having 100% PMM activity) as well as from the CDG-Ia fibroblasts (having 10% PMM activity) and the amounts of the LLO structures were compared using chromatographic methods.

CDG-Ia dermal fibroblasts make a series of truncated lipid-linked oligosaccharide (LLO) species ranging in size from $M_2Gn_2$ to $M_5Gn_2$ with $M_2Gn_2$ and $M_3Gn_2$ being predominant. The M1P liposomes from Example 1 were tested in order to evaluate their capacity to normalize the distribution of various LLO oligosaccharides. CDG-Ia fibroblasts cultured in low glucose DMEM media were incubated with 300 μM of bare M1P (M1P) and 300 μM of the M1P-liposomes (M1PL). After treatment, cells were harvested and LLO oligosaccharides were recovered, hydrolyzed, modified with fluorophore, and analyzed by normal phase chromatography as described by Gao et al. (*Methods in Enzymology*, 2006, 415, 3-20) and Bones et al. (*Anal. Chem*, 2011, 83 (13), 5344-52). The peak area of each LLO was normalized to protein content prior to calculation of percentage abundance.

The results are depicted in Table 2. The distribution of various LLO oligosaccharides from wild-type fibroblasts ranged from $M_2Gn_2$ to $M_7Gn_2$. Treatment of CDG-Ia fibroblasts with M1P-liposomes inhibited the synthesis of truncated LLO oligosaccharides $M_2\ Gn_2$ and $M_3Gn_2$, and shifted production towards larger LLO oligosaccharide species causing an increase in expression of $M_5Gn_2$-$M_7Gn_2$ structures (Table 2). The amount of $M_5Gn_2$ LLO produced after treatment of CDG-Ia fibroblasts with M1P-liposomes was three times greater than the amount in untreated CDG-Ia fibroblasts, and twice the amount in CDG-Ia fibroblasts treated with bare M1P (Table 2). Additionally, higher order LLO oligosaccharides (e.g., $M_6\ Gn_2$ and $M_7Gn_2$) were observed in CDG-Ia fibroblasts after treatment with M1P-liposomes (Table 2). Such higher order LLO oligosaccharides were not observed in the CDG-Ia fibroblasts prior to treatment with M1P-liposomes. Moreover, the amount of $M_6Gn_2$ and $M_7Gn_2$LLO oligosaccharides in CDG-Ia fibroblasts after treatment with M1P-liposomes was comparable to the amount in wild-type fibroblasts (Table 2).

Complete normalization was not observed in all cases, as the analytical approach that was utilized detected both newly synthesized LLO oligosaccharides and LLO oligosaccharides previously produced in the cell.

TABLE 2

| Genotype | Treatment | $M_2Gn_2$ | $M_3Gn_2$ | $M_4Gn_2$ | $M_5Gn_2$ | $M_6Gn_2$ | $M_7Gn_2$ |
|---|---|---|---|---|---|---|---|
| Normal | None | 18 | 10 | 36 | 32 | 4.5 | 0.4 |
| CDG-Ia | None | 31 | 38 | 24 | 6.2 | | |
| CDG-Ia | 300 μM M1PL | 18 | 28 | 31 | 18 | 3.9 | 0.5 |
| CDG-Ia | 300 μM M1P | 40 | 24 | 27 | 8.9 | | |

Table 2 depicts normal phase chromatography analyses of LLO oligosaccharide distribution (expressed as percentage, %) in wild-type fibroblasts and CDG-Ia fibroblasts. The LLO oligosaccharides contain two or more mannose (Man) subunits and an N-acetylglucosamine disaccharide (GlcNAc2). In Table 2, "$M_2Gn_2$" corresponds to Man2GlcNAc2, "$M_3Gn_2$" corresponds to Man3GlcNAc2, "$M_4Gn_2$" corresponds to Man4GlcNAc2, "$M_5Gn_2$" corresponds to Man5GlcNAc2, "$M_6Gnc_2$" corresponds to Man6GlcNAc2, and "$M_7Gn_2$" corresponds to Man7GlcNAc2.

What is claimed is:

1. A composition comprising:
   (i) a lipid particle, wherein the lipid particle comprises phospholipids and polyethylene glycol (PEG),
      wherein at least two of the phospholipids are phosphatidylethanolamine (PE) and phosphatidylcholine (PC), and
      wherein the PEG is conjugated to at least one phospholipid; and
   (ii) an endogenous carbohydrate selected from the group consisting of a phosphorylated mannose, a phosphorylated mannofuranose, and a phosphorylated mannopyranos, and
      wherein the endogenous carbohydrate is encapsulated in the lipid particle.

2. The composition of claim 1, wherein the PE is present at a concentration of up to 50 molar percent.

3. The composition of claim 1, wherein the PC is present at a concentration of up to 50 molar percent.

4. The composition of claim 1, wherein the at least one phospholipid conjugated to PEG is 1,2-distearoyl-sn-glycero-3-phosphoethanolamine (DSPE).

5. The composition of claim 4, wherein the DSPE is present at a concentration of about 3 molar percent.

6. The composition of claim 4, wherein
   the PE is present at a concentration of about 50 molar percent;
   the PC is present at a concentration of about 50 molar percent; and the DSPE conjugated to PEG is present at a concentration of about 3 molar percent.

7. The composition of claim 1, wherein the endogenous carbohydrate is mannose-1-phosphate.

8. The composition of claim 1, wherein the lipid particle comprises
phosphatidylethanolamine (PE) present at a concentration of about 50 molar percent;
phosphatidylcholine (PC) present at a concentration of about 50 molar percent; and
1,2-distearoyl-sn-glycero-3-phosphoethanolamine (DSPE) attached to PEG, wherein the
DSPE conjugated to PEG is present at a concentration of about 3 molar percent; and wherein the endogenous carbohydrate is mannose-1-phosphate.

9. The composition of claim 1, wherein the composition, when administered to a subject in need thereof, induces at least a 0.05-fold to at least a 3-fold increase in cellular production of higher-order lipid-linked oligosaccharides in the subject, as compared to cellular production of higher-order lipid-linked oligosaccharides in the subject in the absence of administering the composition to the subject.

10. A pharmaceutical composition comprising the composition of claim 1, and a pharmaceutically acceptable carrier.

11. The composition of claim 1, wherein the PE is present at a concentration of up to 80 molar percent.

12. The composition of claim 1, wherein the PC is present at a concentration of up to 70 molar percent.

13. The composition of claim 4, wherein the DSPE is present at a concentration of about 5 molar percent.

14. The composition of claim 4, wherein
the PE is present at a concentration of about 30 molar percent;
the PC is present at a concentration of about 70 molar percent; and
the DSPE conjugated to PEG is present at a concentration of about 3 molar percent.

15. The composition of claim 14, wherein the endogenous carbohydrate is mannose-1-phosphate.

16. The composition of claim 1, wherein the endogenous carbohydrate is a phosphorylated mannose.

17. The composition of claim 1, wherein the lipid particle is a liposome.

18. The composition of claim 17, wherein the endogenous carbohydrate is mannose-1-phosphate.

19. A method for delivering a carbohydrate to the interior of a cell, comprising administering to the cell the composition of claim 1, wherein the administered composition traverses the cell plasma membrane to deliver the carbohydrate to the interior of the cell.

20. A method for delivering a carbohydrate to a subject in need thereof, comprising administering to the subject the composition of claim 1.

21. A method for treating a congenital disorder of glycosylation (CDG) in a subject in need thereof, comprising administering to the subject the composition of claim 1.

22. The method of claim 21, wherein the congenital disorder of glycosylation (CDG) is a CDG-Ia disorder.

23. The method of claim 19, wherein administration of the composition induces at least a 0.05-fold to at least a 3-fold increase in cellular production of higher-order lipid-linked oligosaccharides in the interior of the cell, as compared to cellular production of higher-order lipid-linked oligosaccharides in the interior of the cell in the absence of administering the composition to the cell.

* * * * *